(12) United States Patent
Stone

(10) Patent No.: US 9,078,644 B2
(45) Date of Patent: Jul. 14, 2015

(54) FRACTURE FIXATION DEVICE

(75) Inventor: Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 502 days.

(21) Appl. No.: 12/719,337

(22) Filed: Mar. 8, 2010

(65) Prior Publication Data

US 2010/0211075 A1 Aug. 19, 2010

Related U.S. Application Data

(63) Continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, (Continued)

(51) Int. Cl.

| A61B 17/82 | (2006.01) |
|---|---|
| A61B 17/04 | (2006.01) |
| A61B 17/70 | (2006.01) |
| A61B 17/84 | (2006.01) |
| A61B 17/86 | (2006.01) |
| A61B 17/68 | (2006.01) |
| A61B 17/80 | (2006.01) |
| A61B 17/06 | (2006.01) |

(52) U.S. Cl.
CPC ......... *A61B 17/0401* (2013.01); *A61B 17/7053* (2013.01); *A61B 17/82* (2013.01); *A61B 17/842* (2013.01); *A61B 17/8685* (2013.01); *A61B 17/683* (2013.01); *A61B 17/8061* (2013.01); *A61B 2017/0404* (2013.01); *A61B 2017/044* (2013.01); *A61B 2017/0406* (2013.01); *A61B 2017/0417* (2013.01); *A61B 2017/0458* (2013.01); *A61B 2017/06185* (2013.01)

(58) Field of Classification Search
CPC .. A61B 17/82; A61B 17/842; A61B 17/7053; A61B 17/8061
USPC .................. 623/13.11–13.2; 606/280, 70, 71, 606/281–299, 228, 232, 233, 74
See application file for complete search history.

(56) References Cited

U.S. PATENT DOCUMENTS

| 26,501 A | 12/1859 | Kendrick et al. |
|---|---|---|
| 65,499 A | 6/1867 | Miller |

(Continued)

FOREIGN PATENT DOCUMENTS

| AU | 4957264 | 3/1966 |
|---|---|---|
| AU | 440266 | 10/1967 |

(Continued)

OTHER PUBLICATIONS

International Search Report and Written Opinion mailed Feb. 6, 2013 for PCT/US2012/064832 which claims benefit of U.S. Appl. No. 13/295,126 filed Nov. 14, 2011.

(Continued)

*Primary Examiner* — Matthew Lawson
*Assistant Examiner* — Zade Coley
(74) *Attorney, Agent, or Firm* — Harness, Dickey

(57) ABSTRACT

Assemblies for securing a fractured or weakened bone within a subject's body are provided. The assembly includes a frame having an adjustable flexible member construct thereon. The adjustable flexible member construct is disposed in the frame such that the adjustable flexible member and the frame encircle the fractured or weakened bone.

26 Claims, 12 Drawing Sheets

Related U.S. Application Data now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165, application No. 12/719,337, which is a continuation-in-part of application No. 12/570,854, filed on Sep. 30, 2009, now Pat. No. 8,303,604, which is a continuation-in-part of application No. 12/014,399, filed on Jan. 15, 2008, now Pat. No. 7,909,851, application No. 12/719,337, which is a continuation-in-part of application No. 12/702,067, filed on Feb. 8, 2010, now Pat. No. 8,672,968, which is a continuation-in-part of application No. 11/541,505, filed on Sep. 29, 2006, now Pat. No. 7,658,751, application No. 12/719,337, which is a continuation-in-part of application No. 12/196,398, filed on Aug. 22, 2008, now Pat. No. 7,959,650, which is a continuation-in-part of application No. 11/784,821, filed on Apr. 10, 2007.

(56) References Cited

U.S. PATENT DOCUMENTS

| | | | |
|---|---|---|---|
| 126,366 | A | 4/1872 | Wills |
| 233,475 | A | 10/1880 | Cook et al. |
| 261,501 | A | 7/1882 | Vandermark |
| 268,407 | A | 12/1882 | Hughes |
| 330,087 | A | 11/1885 | Binns |
| 394,739 | A * | 12/1888 | Toulmin ............ 24/18 |
| 417,805 | A | 12/1889 | Beaman |
| 487,304 | A | 12/1892 | Todd |
| 762,710 | A | 6/1901 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,635,066 | A | 7/1927 | Wells |
| 401,677 | A | 11/1933 | Roeder |
| 1,950,799 | A | 3/1934 | Jones |
| 2,065,659 | A | 12/1936 | Cullen |
| 2,108,206 | A | 2/1938 | Meeker |
| 2,121,193 | A | 6/1938 | Hanicke |
| 2,242,003 | A | 5/1941 | Lorenzo |
| 2,267,925 | A | 12/1941 | Johnston |
| 2,302,986 | A | 11/1942 | Vollrath |
| 2,329,398 | A | 9/1943 | Duffy |
| 2,397,216 | A | 3/1946 | Stellin |
| RE22,857 | E | 3/1947 | Ogburn |
| 2,526,959 | A | 10/1950 | Lorenzo |
| 2,528,456 | A | 10/1950 | Stevenson |
| 2,562,419 | A | 7/1951 | Ferris |
| 2,581,564 | A | 1/1952 | Villegas |
| 2,600,395 | A | 6/1952 | Domoj et al. |
| 2,610,631 | A | 9/1952 | Calicchio |
| 2,665,597 | A | 1/1954 | Hill |
| 2,669,774 | A | 2/1954 | Mitchell |
| 2,698,986 | A | 1/1955 | Brown |
| 2,760,488 | A | 8/1956 | Pierce |
| 2,833,284 | A | 5/1958 | Springer |
| 2,846,712 | A | 8/1958 | Markman |
| 2,860,393 | A | 11/1958 | Brock |
| 2,880,728 | A | 4/1959 | Rights |
| 2,881,762 | A | 4/1959 | Lowrie |
| 2,883,096 | A | 4/1959 | Dawson |
| 2,913,042 | A | 11/1959 | Taylor |
| 3,000,009 | A | 9/1961 | Selstad |
| 3,003,155 | A | 10/1961 | Mielzynski et al. |
| 3,013,559 | A | 12/1961 | Thomas |
| 3,037,619 | A | 6/1962 | Stevans |
| 3,039,460 | A | 6/1962 | Chandler |
| 3,081,781 | A * | 3/1963 | Stermer ............ 132/273 |
| 3,090,386 | A | 5/1963 | Curtis |
| 3,103,666 | A | 9/1963 | Bone |
| 3,123,077 | A | 3/1964 | Alcamo |
| 3,125,095 | A | 3/1964 | Kaufman et al. |
| 3,209,422 | A | 10/1965 | Dritz |
| 3,234,938 | A | 2/1966 | Robinson |
| 3,240,379 | A | 3/1966 | Bremer et al. |
| 3,250,271 | A | 5/1966 | Lippes |
| 3,399,432 | A | 9/1968 | Merser |
| 3,409,014 | A | 11/1968 | Shannon |
| 3,435,475 | A | 4/1969 | Bisk |
| 3,467,089 | A | 9/1969 | Hasson |
| 3,470,834 | A | 10/1969 | Bone |
| 3,470,875 | A | 10/1969 | Johnson |
| 3,500,820 | A | 3/1970 | Almen |
| 3,507,274 | A | 4/1970 | Soichet |
| 3,513,484 | A | 5/1970 | Hausner |
| 3,515,132 | A | 6/1970 | McKnight |
| 3,522,803 | A | 8/1970 | Majzlin |
| 3,527,223 | A | 9/1970 | Shein |
| 3,533,406 | A | 10/1970 | Hutterer et al. |
| 3,541,591 | A | 11/1970 | Hoegerman |
| 3,547,389 | A | 12/1970 | Mitchell |
| 3,579,831 | A | 5/1971 | Stevens et al. |
| 3,590,616 | A | 7/1971 | Schussler et al. |
| 3,608,095 | A | 9/1971 | Barry |
| 3,618,447 | A | 11/1971 | Goins |
| 3,628,530 | A | 12/1971 | Schwartz |
| 3,643,649 | A | 2/1972 | Amato |
| 3,648,705 | A | 3/1972 | Lary |
| 3,656,483 | A | 4/1972 | Rudel |
| 3,659,597 | A | 5/1972 | Wolfers |
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner, Jr. |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,807,407 | A | 4/1974 | Schweizer |
| 3,810,456 | A | 5/1974 | Karman |
| 3,825,010 | A | 7/1974 | McDonald |
| 3,840,017 | A | 10/1974 | Violante et al. |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |
| 3,896,500 | A | 7/1975 | Rambert et al. |
| 3,907,442 | A | 9/1975 | Reid |
| 3,910,281 | A | 10/1975 | Kletschka et al. |
| 3,918,444 | A | 11/1975 | Hoff et al. |
| 3,918,455 | A | 11/1975 | Coplan |
| 3,927,666 | A | 12/1975 | Hoff |
| 3,931,667 | A | 1/1976 | Merser et al. |
| 3,933,153 | A | 1/1976 | Csatary et al. |
| 3,937,217 | A | 2/1976 | Kosonen et al. |
| 3,943,932 | A | 3/1976 | Woo |
| 3,946,446 | A | 3/1976 | Schofield |
| 3,946,728 | A | 3/1976 | Bettex |

(56) References Cited

U.S. PATENT DOCUMENTS

| | | | |
|---|---|---|---|
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,146,022 A * | 3/1979 | Johnson et al. ............. 606/74 |
| 4,149,277 A | 4/1979 | Bokros |
| 4,157,714 A | 6/1979 | Foltz et al. |
| 4,158,250 A * | 6/1979 | Ringwald ................. 24/16 R |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,490 A * | 6/1981 | Bivins ..................... 27/21.1 |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov |
| 4,326,531 A | 4/1982 | Shimonaka |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,489,464 A * | 12/1984 | Massari et al. ............. 24/279 |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A * | 5/1987 | Davis ..................... 606/233 |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson et al. |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |

(56) References Cited

U.S. PATENT DOCUMENTS

| | | | |
|---|---|---|---|
| 4,860,513 A | 8/1989 | Whitman | |
| 4,863,383 A | 9/1989 | Grafelmann et al. | |
| 4,870,957 A | 10/1989 | Goble et al. | |
| 4,873,976 A | 10/1989 | Schreiber | |
| 4,887,601 A | 12/1989 | Richards | |
| 4,889,110 A * | 12/1989 | Galline et al. | 606/916 |
| 4,890,615 A | 1/1990 | Caspari et al. | |
| 4,893,619 A | 1/1990 | Dale et al. | |
| 4,893,974 A | 1/1990 | Fischer et al. | |
| 4,895,148 A | 1/1990 | Bays et al. | |
| 4,896,668 A | 1/1990 | Popoff et al. | |
| 4,898,156 A | 2/1990 | Gatturna et al. | |
| 4,899,743 A | 2/1990 | Nicholson et al. | |
| 4,901,721 A | 2/1990 | Hakki | |
| 4,923,461 A | 5/1990 | Caspari et al. | |
| 4,927,421 A | 5/1990 | Goble et al. | |
| 4,946,377 A | 8/1990 | Kovach | |
| 4,946,468 A | 8/1990 | Li | |
| 4,950,270 A | 8/1990 | Bowman et al. | |
| 4,950,285 A | 8/1990 | Wilk | |
| 4,960,381 A | 10/1990 | Niznick | |
| 4,961,741 A | 10/1990 | Hayhurst | |
| 4,968,315 A | 11/1990 | Gatturna | |
| 4,968,317 A | 11/1990 | Tormala et al. | |
| 4,969,886 A | 11/1990 | Cziffer et al. | |
| 4,976,736 A | 12/1990 | White et al. | |
| 4,978,350 A | 12/1990 | Wagenknecht et al. | |
| 4,979,956 A | 12/1990 | Silvestrini | |
| 4,983,176 A | 1/1991 | Cushman et al. | |
| 4,988,351 A | 1/1991 | Paulos et al. | |
| 4,994,074 A | 2/1991 | Bezwada et al. | |
| 4,997,433 A | 3/1991 | Goble et al. | |
| 5,002,550 A | 3/1991 | Li | |
| 5,002,562 A | 3/1991 | Oberlander | |
| 5,007,921 A | 4/1991 | Brown | |
| 5,030,224 A | 7/1991 | Wright et al. | |
| 5,030,235 A | 7/1991 | Campbell, Jr. | |
| 5,037,422 A | 8/1991 | Hayhurst et al. | |
| 5,041,129 A | 8/1991 | Hayhurst et al. | |
| 5,046,513 A | 9/1991 | Gatturna et al. | |
| 5,047,030 A | 9/1991 | Draenert | |
| 5,053,046 A | 10/1991 | Janese | |
| 5,053,047 A | 10/1991 | Yoon | |
| 5,059,201 A | 10/1991 | Asnis | |
| 5,059,206 A | 10/1991 | Winters | |
| 5,061,277 A | 10/1991 | Carpentier et al. | |
| 5,062,344 A | 11/1991 | Gerker | |
| 5,062,843 A | 11/1991 | Mahony, III | |
| 5,064,431 A | 11/1991 | Gilbertson et al. | |
| 5,074,874 A | 12/1991 | Yoon et al. | |
| 5,078,731 A | 1/1992 | Hayhurst | |
| 5,078,843 A | 1/1992 | Pratt | |
| 5,084,050 A | 1/1992 | Draenert | |
| 5,084,058 A | 1/1992 | Li | |
| 5,085,661 A | 2/1992 | Moss | |
| 5,087,263 A | 2/1992 | Li | |
| 5,089,012 A | 2/1992 | Prou | |
| 5,092,866 A | 3/1992 | Breard et al. | |
| 5,098,435 A | 3/1992 | Stednitz et al. | |
| 5,100,415 A | 3/1992 | Hayhurst | |
| 5,100,417 A | 3/1992 | Cerier et al. | |
| 5,116,337 A | 5/1992 | Johnson | |
| 5,116,373 A | 5/1992 | Jakob et al. | |
| 5,116,375 A | 5/1992 | Hofmann | |
| 5,123,913 A | 6/1992 | Wilk et al. | |
| 5,123,914 A | 6/1992 | Cope | |
| 5,127,785 A | 7/1992 | Faucher et al. | |
| 5,129,901 A | 7/1992 | Decoste | |
| 5,129,902 A | 7/1992 | Goble et al. | |
| 5,129,904 A | 7/1992 | Illi et al. | |
| 5,129,906 A | 7/1992 | Ross et al. | |
| 5,139,498 A | 8/1992 | Astudillo Ley | |
| 5,139,499 A | 8/1992 | Small et al. | |
| 5,139,520 A | 8/1992 | Rosenberg | |
| 5,143,498 A | 9/1992 | Whitman | |
| 5,147,362 A | 9/1992 | Goble | |
| 5,149,329 A | 9/1992 | Richardson | |
| 5,151,104 A | 9/1992 | Kenna | |
| 5,152,790 A | 10/1992 | Rosenberg et al. | |
| 5,154,189 A | 10/1992 | Oberlander | |
| 5,156,616 A | 10/1992 | Meadows et al. | |
| 5,163,960 A | 11/1992 | Bonutti | |
| D331,626 S | 12/1992 | Hayhurst et al. | |
| 5,169,400 A | 12/1992 | Muhling et al. | |
| 5,176,682 A | 1/1993 | Chow | |
| 5,178,629 A | 1/1993 | Kammerer | |
| 5,183,458 A | 2/1993 | Marx | |
| 5,190,545 A * | 3/1993 | Corsi et al. | 606/74 |
| 5,192,282 A | 3/1993 | Draenert et al. | |
| 5,197,987 A | 3/1993 | Koch et al. | |
| 5,199,135 A * | 4/1993 | Gold | 24/16 R |
| 5,203,784 A | 4/1993 | Ross et al. | |
| 5,203,787 A | 4/1993 | Noblitt et al. | |
| 5,207,679 A | 5/1993 | Li | |
| 5,209,753 A | 5/1993 | Biedermann et al. | |
| 5,209,805 A | 5/1993 | Spraggins | |
| 5,211,647 A | 5/1993 | Schmieding | |
| 5,211,650 A | 5/1993 | Noda | |
| 5,214,987 A | 6/1993 | Fenton, Sr. | |
| 5,219,359 A | 6/1993 | McQuilkin et al. | |
| 5,222,976 A | 6/1993 | Yoon | |
| 5,224,946 A | 7/1993 | Hayhurst et al. | |
| 5,230,699 A | 7/1993 | Grasinger | |
| 5,232,436 A | 8/1993 | Janevski | |
| 5,234,435 A | 8/1993 | Seagrave, Jr. | |
| 5,235,238 A | 8/1993 | Nomura et al. | |
| 5,236,445 A | 8/1993 | Hayhurst et al. | |
| 5,236,461 A | 8/1993 | Forte | |
| 5,242,447 A | 9/1993 | Borzone | |
| 5,246,441 A | 9/1993 | Ross et al. | |
| 5,249,899 A | 10/1993 | Wilson | |
| 5,250,053 A | 10/1993 | Snyder | |
| 5,258,015 A | 11/1993 | Li et al. | |
| 5,258,016 A | 11/1993 | DiPoto et al. | |
| 5,258,040 A | 11/1993 | Bruchman et al. | |
| 5,261,908 A | 11/1993 | Campbell, Jr. | |
| 5,268,001 A | 12/1993 | Nicholson et al. | |
| 5,269,160 A | 12/1993 | Wood | |
| 5,269,783 A | 12/1993 | Sander | |
| 5,269,806 A | 12/1993 | Sardelis et al. | |
| 5,269,809 A | 12/1993 | Hayhurst et al. | |
| 5,279,311 A | 1/1994 | Snyder | |
| 5,281,422 A | 1/1994 | Badylak et al. | |
| 5,282,809 A | 2/1994 | Kammerer et al. | |
| 5,282,832 A | 2/1994 | Toso et al. | |
| 5,282,867 A | 2/1994 | Mikhail | |
| 5,285,040 A | 2/1994 | Brandberg et al. | |
| 5,290,217 A | 3/1994 | Campos | |
| 5,290,243 A | 3/1994 | Chodorow et al. | |
| 5,306,301 A | 4/1994 | Graf et al. | |
| 5,312,422 A | 5/1994 | Trott | |
| 5,312,438 A | 5/1994 | Johnson | |
| 5,318,566 A | 6/1994 | Miller | |
| 5,318,575 A | 6/1994 | Chesterfield et al. | |
| 5,318,577 A | 6/1994 | Li | |
| 5,318,578 A | 6/1994 | Hasson | |
| 5,320,115 A | 6/1994 | Kenna | |
| 5,320,626 A | 6/1994 | Schmieding | |
| 5,320,633 A | 6/1994 | Allen et al. | |
| 5,324,308 A | 6/1994 | Pierce | |
| 5,330,489 A | 7/1994 | Green et al. | |
| 5,333,625 A | 8/1994 | Klein | |
| 5,334,204 A | 8/1994 | Clewett et al. | |
| 5,336,229 A | 8/1994 | Noda | |
| 5,336,231 A | 8/1994 | Adair | |
| 5,336,240 A | 8/1994 | Metzler et al. | |
| 5,339,870 A | 8/1994 | Green et al. | |
| 5,342,369 A | 8/1994 | Harryman, II | |
| 5,346,462 A | 9/1994 | Barber | |
| 5,354,292 A | 10/1994 | Braeuer et al. | |
| 5,354,298 A | 10/1994 | Lee et al. | |
| 5,356,412 A | 10/1994 | Golds et al. | |
| 5,356,413 A | 10/1994 | Martins et al. | |
| 5,356,417 A | 10/1994 | Golds | |

(56) References Cited

U.S. PATENT DOCUMENTS

| | | |
|---|---|---|
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,379,492 A | 1/1995 | Glesser |
| 5,383,878 A | 1/1995 | Roger et al. |
| 5,383,904 A | 1/1995 | Totakura et al. |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A * | 5/1995 | Kilpela et al. ............... 606/300 |
| 5,417,690 A * | 5/1995 | Sennett et al. ............... 606/74 |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,736 A | 4/1996 | Reimels et al. |
| 5,507,754 A | 4/1996 | Green et al. |
| 5,520,691 A | 5/1996 | Branch |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,571,090 A | 11/1996 | Sherts |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A * | 3/1997 | Bailey ............................ 606/74 |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |

(56) References Cited

U.S. PATENT DOCUMENTS

| | | |
|---|---|---|
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,285 A | 11/1997 | Yamada et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,904 A | 2/1998 | Errico et al. |
| 5,713,905 A | 2/1998 | Goble et al. |
| 5,713,921 A | 2/1998 | Bonutti |
| 5,715,578 A * | 2/1998 | Knudson .................... 24/16 PB |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Brånemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A * | 4/1998 | Chan .................... 606/74 |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,830,234 A | 11/1998 | Wojciechowicz et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A * | 12/1998 | Abboudi .................... 606/57 |
| 5,860,973 A | 1/1999 | Michelson |
| 5,868,740 A | 2/1999 | LeVeen et al. |
| 5,868,748 A | 2/1999 | Burke |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |

(56) References Cited

U.S. PATENT DOCUMENTS

| | | |
|---|---|---|
| 5,968,045 A | 10/1999 | Frazier |
| 5,968,047 A | 10/1999 | Reed |
| 5,968,077 A | 10/1999 | Wojciechowicz et al. |
| 5,972,006 A | 10/1999 | Sciaino, Jr. |
| 5,976,125 A | 11/1999 | Graham |
| 5,976,127 A | 11/1999 | Lax |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex et al. |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger et al. |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,106,545 A | 8/2000 | Egan |
| 6,110,128 A | 8/2000 | Andelin et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom et al. |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |

(56) References Cited

U.S. PATENT DOCUMENTS

| | | |
|---|---|---|
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex et al. |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein et al. |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,543,094 B2 * | 4/2003 | D'Addario ............... 24/16 PB |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B2 | 11/2003 | Lizardi |
| 6,641,597 B2 | 11/2003 | Burkhart et al. |
| 6,645,211 B2 | 11/2003 | Magana |
| 6,645,227 B2 | 11/2003 | Fallin et al. |
| 6,652,450 B2 | 11/2003 | Neisz et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,533 B1 * | 1/2004 | Dinsdale et al. ............... 606/74 |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,793,595 B1 * | 9/2004 | Monnet ............... 473/478 |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |

(56) References Cited

U.S. PATENT DOCUMENTS

| | | |
|---|---|---|
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 7,001,429 B2 | 2/2006 | Ferguson |
| 7,004,959 B2 | 2/2006 | Bonutti |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,333 B2 | 1/2007 | Plouhar et al. |
| 7,201,722 B2 | 4/2007 | Krueger |
| 7,207,993 B1 * | 4/2007 | Baldwin et al. ............ 606/70 |
| 7,255,675 B2 | 8/2007 | Gertner et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,303,577 B1 | 12/2007 | Dean |
| 7,306,417 B2 | 12/2007 | Dorstewitz |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,494,506 B2 | 2/2009 | Brulez et al. |
| 7,500,983 B1 | 3/2009 | Kaiser et al. |
| 7,513,910 B2 | 4/2009 | Buskirk et al. |
| 7,578,825 B2 | 8/2009 | Huebner |
| 7,585,311 B2 | 9/2009 | Green et al. |
| 7,591,823 B2 | 9/2009 | Tipirneni |
| 7,601,165 B2 | 10/2009 | Stone |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,695,503 B1 | 4/2010 | Kaiser et al. |
| 7,717,929 B2 | 5/2010 | Fallman |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,776,041 B1 | 8/2010 | Walters |
| 7,819,895 B2 | 10/2010 | Ginn et al. |
| 7,856,698 B2 * | 12/2010 | Hays ............................ 24/129 R |
| 7,857,830 B2 | 12/2010 | Stone et al. |
| 7,867,264 B2 | 1/2011 | McDevitt et al. |
| 7,875,058 B2 | 1/2011 | Holmes, Jr. |
| 7,878,058 B2 | 2/2011 | Blendinger et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,836 B2 | 2/2012 | Denham et al. |
| 8,128,658 B2 | 3/2012 | Kaiser et al. |
| 8,137,354 B2 | 3/2012 | Stone |
| 8,137,382 B2 | 3/2012 | Denham et al. |
| 8,167,906 B2 | 5/2012 | Cauldwell et al. |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,273,106 B2 | 9/2012 | Stone et al. |
| 8,292,921 B2 | 10/2012 | Stone et al. |
| 8,298,284 B2 | 10/2012 | Cassani |
| 8,337,525 B2 | 12/2012 | Stone et al. |
| 8,343,155 B2 * | 1/2013 | Fisher et al. ............ 606/74 |
| 8,343,227 B2 | 1/2013 | Metzger et al. |
| 8,361,113 B2 | 1/2013 | Stone et al. |
| 8,409,253 B2 | 4/2013 | Stone et al. |
| 8,486,114 B2 * | 7/2013 | Gillard et al. ............ 606/280 |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,969 B2 | 3/2014 | Stone et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,840,645 B2 | 9/2014 | Denham et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 * | 11/2001 | Hein ............................ 623/13.13 |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |

(56) References Cited

U.S. PATENT DOCUMENTS

| | | |
|---|---|---|
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0068254 A1* | 6/2002 | Campbell ............... 433/18 |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1* | 10/2002 | Lerch et al. ............... 606/70 |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1* | 11/2002 | Chervitz et al. ............... 606/74 |
| 2002/0188298 A1 | 12/2002 | Chan |
| 2002/0193830 A1 | 12/2002 | Bonutti |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0070928 A1 | 3/2005 | Heino et al. |
| 2005/0074495 A1 | 4/2005 | Schwartz et al. |
| 2005/0076478 A1* | 4/2005 | Miyazaki et al. ........... 24/16 PB |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |

(56) References Cited

U.S. PATENT DOCUMENTS

| | | |
|---|---|---|
| 2005/0124996 A1 | 6/2005 | Hearn |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149266 A1 | 7/2006 | Cordasco |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0229671 A1 | 10/2006 | Steiner et al. |
| 2006/0235407 A1* | 10/2006 | Wang et al. ............... 606/69 |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1* | 12/2006 | Fallin et al. ............. 623/16.11 |
| 2006/0280768 A1 | 12/2006 | Hwang et al. |
| 2006/0282082 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0219558 A1 | 9/2007 | Deutsch |
| 2007/0225719 A1 | 9/2007 | Stone et al. |
| 2007/0233241 A1 | 10/2007 | Graf et al. |
| 2007/0239209 A1 | 10/2007 | Fallman |
| 2007/0239275 A1 | 10/2007 | Willobee |
| 2007/0250059 A1* | 10/2007 | Weisshaupt et al. ............ 606/60 |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2008/0027446 A1 | 1/2008 | Stone et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1* | 4/2008 | Stone ........................... 606/232 |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0161852 A1 | 7/2008 | Kaiser et al. |
| 2008/0161861 A1 | 7/2008 | Huebner |
| 2008/0172097 A1 | 7/2008 | Lerch et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0300611 A1 | 12/2008 | Houser et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0054928 A1 | 2/2009 | Denham et al. |

(56) References Cited

U.S. PATENT DOCUMENTS

| | | | |
|---|---|---|---|
| 2009/0062854 A1 | 3/2009 | Kaiser et al. | |
| 2009/0082790 A1 | 3/2009 | Shad et al. | |
| 2009/0082805 A1 | 3/2009 | Kaiser et al. | |
| 2009/0099598 A1 | 4/2009 | McDevitt et al. | |
| 2009/0105717 A1* | 4/2009 | Bluechel | 606/103 |
| 2009/0105754 A1 | 4/2009 | Sethi | |
| 2009/0118774 A1 | 5/2009 | Miller, III | |
| 2009/0118775 A1 | 5/2009 | Burke | |
| 2009/0125073 A1 | 5/2009 | Rehm | |
| 2009/0138002 A1 | 5/2009 | Fenton | |
| 2009/0138054 A1 | 5/2009 | Teague et al. | |
| 2009/0156997 A1 | 6/2009 | Trenhaile | |
| 2009/0163949 A1 | 6/2009 | Rolnick et al. | |
| 2009/0177233 A1 | 7/2009 | Malek | |
| 2009/0192468 A1 | 7/2009 | Stone | |
| 2009/0198277 A1 | 8/2009 | Gordon et al. | |
| 2009/0204146 A1 | 8/2009 | Kaiser et al. | |
| 2009/0228042 A1 | 9/2009 | Koogle, Jr. et al. | |
| 2009/0234357 A1 | 9/2009 | Morales et al. | |
| 2009/0234358 A1 | 9/2009 | Morales et al. | |
| 2009/0240251 A1 | 9/2009 | Gabele | |
| 2009/0248091 A1 | 10/2009 | Teague et al. | |
| 2009/0265014 A1 | 10/2009 | May et al. | |
| 2009/0287215 A1* | 11/2009 | Fisher et al. | 606/71 |
| 2009/0306711 A1 | 12/2009 | Stone et al. | |
| 2009/0312776 A1 | 12/2009 | Kaiser et al. | |
| 2009/0318960 A1 | 12/2009 | Burkhart | |
| 2009/0318961 A1 | 12/2009 | Stone et al. | |
| 2010/0042114 A1 | 2/2010 | Schaffhausen | |
| 2010/0087857 A1 | 4/2010 | Stone et al. | |
| 2010/0145384 A1 | 6/2010 | Stone et al. | |
| 2010/0191342 A1 | 7/2010 | Byrd et al. | |
| 2010/0211071 A1* | 8/2010 | Lettmann et al. | 606/60 |
| 2010/0211075 A1 | 8/2010 | Stone | |
| 2010/0256677 A1 | 10/2010 | Albertorio et al. | |
| 2010/0268273 A1 | 10/2010 | Albertorio et al. | |
| 2010/0268275 A1 | 10/2010 | Stone et al. | |
| 2010/0270306 A1 | 10/2010 | Shiffer | |
| 2010/0292792 A1 | 11/2010 | Stone et al. | |
| 2010/0305698 A1 | 12/2010 | Metzger et al. | |
| 2010/0305709 A1 | 12/2010 | Metzger et al. | |
| 2010/0312341 A1 | 12/2010 | Kaiser et al. | |
| 2011/0009885 A1 | 1/2011 | Graf et al. | |
| 2011/0022083 A1 | 1/2011 | DiMatteo et al. | |
| 2011/0026141 A1 | 2/2011 | Barrows | |
| 2011/0046733 A1 | 2/2011 | Eggli | |
| 2011/0087284 A1 | 4/2011 | Stone et al. | |
| 2011/0098727 A1 | 4/2011 | Kaiser et al. | |
| 2011/0106153 A1 | 5/2011 | Stone et al. | |
| 2011/0112537 A1 | 5/2011 | Bernstein et al. | |
| 2011/0112538 A1* | 5/2011 | Dell'Oca | 606/74 |
| 2011/0160767 A1 | 6/2011 | Stone et al. | |
| 2011/0160768 A1 | 6/2011 | Stone et al. | |
| 2011/0208239 A1 | 8/2011 | Stone et al. | |
| 2011/0208240 A1 | 8/2011 | Stone et al. | |
| 2011/0213416 A1 | 9/2011 | Kaiser | |
| 2011/0218625 A1 | 9/2011 | Berelsman et al. | |
| 2011/0224799 A1 | 9/2011 | Stone | |
| 2011/0245868 A1 | 10/2011 | Teeslink et al. | |
| 2011/0264141 A1 | 10/2011 | Denham et al. | |
| 2011/0270278 A1 | 11/2011 | Overes et al. | |
| 2011/0270306 A1 | 11/2011 | Denham et al. | |
| 2012/0004669 A1 | 1/2012 | Overes et al. | |
| 2012/0041485 A1 | 2/2012 | Kaiser et al. | |
| 2012/0041486 A1 | 2/2012 | Stone et al. | |
| 2012/0046693 A1 | 2/2012 | Denham et al. | |
| 2012/0053630 A1 | 3/2012 | Denham et al. | |
| 2012/0059417 A1 | 3/2012 | Norton et al. | |
| 2012/0059418 A1 | 3/2012 | Denham et al. | |
| 2012/0095470 A1 | 4/2012 | Kaiser et al. | |
| 2012/0109156 A1 | 5/2012 | Overes et al. | |
| 2012/0116409 A1 | 5/2012 | Stone | |
| 2012/0116450 A1 | 5/2012 | McDevitt et al. | |
| 2012/0116452 A1 | 5/2012 | Stone et al. | |
| 2012/0123447 A1 | 5/2012 | Corrao et al. | |
| 2012/0123474 A1 | 5/2012 | Zajac et al. | |
| 2012/0123541 A1 | 5/2012 | Albertorio et al. | |
| 2012/0143215 A1 | 6/2012 | Corrao et al. | |
| 2012/0150223 A1 | 6/2012 | Manos et al. | |
| 2012/0150297 A1 | 6/2012 | Denham et al. | |
| 2012/0165866 A1 | 6/2012 | Kaiser et al. | |
| 2012/0165867 A1 | 6/2012 | Denham et al. | |
| 2012/0165938 A1 | 6/2012 | Denham et al. | |
| 2012/0197271 A1 | 8/2012 | Astorino et al. | |
| 2012/0215257 A1 | 8/2012 | McDevitt et al. | |
| 2012/0290004 A1 | 11/2012 | Lombardo et al. | |
| 2012/0310245 A1 | 12/2012 | Hoeppner et al. | |
| 2013/0018375 A1 | 1/2013 | Dell'Oca | |
| 2013/0018416 A1 | 1/2013 | Lombardo et al. | |
| 2013/0023928 A1 | 1/2013 | Dreyfuss | |
| 2013/0023929 A1 | 1/2013 | Sullivan et al. | |
| 2013/0023930 A1 | 1/2013 | Stone et al. | |
| 2013/0035698 A1 | 2/2013 | Stone et al. | |
| 2013/0035722 A1 | 2/2013 | McDevitt et al. | |
| 2013/0046341 A1 | 2/2013 | Stone et al. | |
| 2013/0103082 A1 | 4/2013 | Kaiser et al. | |
| 2013/0110165 A1 | 5/2013 | Burkhart et al. | |
| 2013/0110251 A1 | 5/2013 | Metzger et al. | |
| 2013/0116730 A1 | 5/2013 | Denham et al. | |
| 2013/0123810 A1 | 5/2013 | Brown et al. | |
| 2013/0123813 A1 | 5/2013 | Stone et al. | |
| 2013/0131722 A1 | 5/2013 | Marchand et al. | |
| 2013/0138123 A1 | 5/2013 | Stone et al. | |
| 2013/0144337 A1 | 6/2013 | Stone et al. | |
| 2013/0144338 A1 | 6/2013 | Stone et al. | |
| 2013/0158601 A1 | 6/2013 | Stone et al. | |
| 2013/0190818 A1 | 7/2013 | Norton | |
| 2013/0190819 A1 | 7/2013 | Norton | |
| 2013/0204276 A1 | 8/2013 | Stone et al. | |
| 2013/0211452 A1 | 8/2013 | Stone et al. | |
| 2013/0237997 A1 | 9/2013 | Arai et al. | |
| 2013/0245761 A1 | 9/2013 | Conner et al. | |
| 2013/0274812 A1 | 10/2013 | Dell'Oca | |
| 2013/0289564 A1 | 10/2013 | Bernstein et al. | |
| 2013/0317621 A1 | 11/2013 | Metzger et al. | |
| 2013/0331848 A1 | 12/2013 | Kaiser et al. | |
| 2014/0046367 A1 | 2/2014 | Stone et al. | |
| 2014/0046368 A1 | 2/2014 | Kaiser et al. | |
| 2014/0067081 A1 | 3/2014 | Stone | |
| 2014/0088655 A1 | 3/2014 | Stone et al. | |
| 2014/0094913 A1 | 4/2014 | Berelsman et al. | |
| 2014/0135835 A1 | 5/2014 | Stone et al. | |
| 2014/0163613 A1 | 6/2014 | Stone et al. | |
| 2014/0163614 A1 | 6/2014 | Denham et al. | |
| 2014/0194927 A1 | 7/2014 | Kaiser et al. | |
| 2014/0200583 A1 | 7/2014 | Stone et al. | |
| 2014/0257378 A1 | 9/2014 | Norton et al. | |
| 2014/0276992 A1 | 9/2014 | Stone et al. | |
| 2014/0277447 A1 | 9/2014 | Berelsman et al. | |
| 2014/0324101 A1 | 10/2014 | Denham et al. | |
| 2014/0330311 A1 | 11/2014 | Denham et al. | |

FOREIGN PATENT DOCUMENTS

| | | |
|---|---|---|
| AU | 2223767 | 11/1968 |
| AU | 5028569 | 8/1970 |
| AU | 5850469 | 1/1971 |
| AU | 5963869 | 2/1971 |
| AU | 1505470 | 11/1971 |
| AU | 3615171 | 5/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |

(56) References Cited

FOREIGN PATENT DOCUMENTS

| | | | |
|---|---|---|---|
| DE | 19841252 | 3/2000 | |
| DE | 20207781 U1 | 8/2002 | |
| EP | 19062 A1 | 11/1980 | |
| EP | 19062 A1 * | 11/1980 | ............ A61B 17/18 |
| EP | 0108912 | 5/1984 | |
| EP | 0129442 | 12/1984 | |
| EP | 0172130 | 2/1986 | |
| EP | 0241240 | 10/1987 | |
| EP | 0241792 | 10/1987 | |
| EP | 0260970 | 3/1988 | |
| EP | 0270704 | 6/1988 | |
| EP | 0282789 | 9/1988 | |
| EP | 0315371 | 5/1989 | |
| EP | 0317406 | 5/1989 | |
| EP | 0340159 | 11/1989 | |
| EP | 0346183 | 12/1989 | |
| EP | 0349173 | 1/1990 | |
| EP | 0374088 | 6/1990 | |
| EP | 0409364 | 1/1991 | |
| EP | 0415915 | 3/1991 | |
| EP | 0440991 | 8/1991 | |
| EP | 0441065 | 8/1991 | |
| EP | 0451932 | 10/1991 | |
| EP | 0464480 | 1/1992 | |
| EP | 0497079 | 8/1992 | |
| EP | 0502509 | 9/1992 | |
| EP | 0502698 | 9/1992 | |
| EP | 520177 | 12/1992 | |
| EP | 0546726 | 6/1993 | |
| EP | 0574707 | 12/1993 | |
| EP | 0582514 | 2/1994 | |
| EP | 0591991 | 4/1994 | |
| EP | 0598219 | 5/1994 | |
| EP | 0611551 A1 | 8/1994 | |
| EP | 0627203 | 12/1994 | |
| EP | 0651979 | 5/1995 | |
| EP | 0669110 | 8/1995 | |
| EP | 0686373 | 12/1995 | |
| EP | 0702933 | 3/1996 | |
| EP | 0775473 | 5/1997 | |
| EP | 0913123 | 5/1999 | |
| EP | 0913131 | 5/1999 | |
| EP | 99121106 | 10/1999 | |
| EP | 991210527 | 10/1999 | |
| EP | 0995409 | 4/2000 | |
| EP | 1013229 | 6/2000 | |
| EP | 1093773 | 4/2001 | |
| EP | 1093774 | 4/2001 | |
| EP | 1555945 | 7/2005 | |
| EP | 2238944 A2 | 10/2010 | |
| EP | 2544607 A1 | 1/2013 | |
| EP | 2709557 A1 | 3/2014 | |
| FR | 2622790 | 5/1989 | |
| FR | 2655840 | 6/1991 | |
| FR | 2682867 | 4/1993 | |
| FR | 2687911 | 9/1993 | |
| FR | 2688689 | 9/1993 | |
| FR | 2704140 | 10/1994 | |
| FR | 2717070 | 9/1995 | |
| FR | 2723528 | 2/1996 | |
| FR | 2744010 | 8/1997 | |
| FR | 2745999 | 9/1997 | |
| FR | 2770764 | 5/1999 | |
| GB | 401677 | 11/1933 | |
| GB | 1413477 | 11/1975 | |
| GB | 1485681 | 9/1977 | |
| GB | 2083751 | 3/1982 | |
| GB | 2118474 | 11/1983 | |
| GB | 2227175 | 7/1990 | |
| GB | 2253147 | 9/1992 | |
| GB | 2312376 | 10/1997 | |
| GB | 2403416 A | 1/2005 | |
| JP | 5362911 | 5/1978 | |
| JP | 5362912 | 5/1978 | |
| JP | 5374942 | 6/1978 | |
| JP | 5378230 | 6/1978 | |
| JP | 62159647 | 7/1987 | |
| JP | 62295657 | 12/1987 | |
| JP | 5269160 | 10/1993 | |
| JP | 5300917 | 11/1993 | |
| JP | 751292 | 2/1995 | |
| JP | 10211213 | 8/1998 | |
| WO | WO-8300615 | 3/1983 | |
| WO | WO-8603666 | 7/1986 | |
| WO | WO-8701270 | 3/1987 | |
| WO | WO-8901767 | 3/1989 | |
| WO | WO-8909030 | 10/1989 | |
| WO | WO-8910096 | 11/1989 | |
| WO | WO-9008510 | 8/1990 | |
| WO | WO-9203980 | 3/1992 | |
| WO | WO-9314705 | 8/1993 | |
| WO | WO-9315694 | 8/1993 | |
| WO | WO-9502373 | 1/1995 | |
| WO | WO-9503003 | 2/1995 | |
| WO | WO-9529637 | 11/1995 | |
| WO | WO-9532670 | 12/1995 | |
| WO | WO-9629029 | 9/1996 | |
| WO | WO-9737603 | 10/1997 | |
| WO | WO-9812991 | 4/1998 | |
| WO | WO-9812992 | 4/1998 | |
| WO | WO-9822047 | 5/1998 | |
| WO | WO-9822048 | 5/1998 | |
| WO | WO-9901084 | 1/1999 | |
| WO | WO-9912480 | 3/1999 | |
| WO | WO-9944544 | 9/1999 | |
| WO | WO-0040159 | 7/2000 | |
| WO | WO-0139671 | 6/2001 | |
| WO | WO-0236020 | 5/2002 | |
| WO | WO-03005914 A1 | 1/2003 | |
| WO | WO-03071962 | 9/2003 | |
| WO | WO-03077772 | 9/2003 | |
| WO | WO-2004091412 A1 | 10/2004 | |
| WO | WO-2005104992 A1 | 11/2005 | |
| WO | WO-2005122954 A1 | 12/2005 | |
| WO | WO-2007103562 A2 | 9/2007 | |
| WO | WO-2008002550 A2 | 1/2008 | |
| WO | WO-2009012021 A1 | 1/2009 | |
| WO | WO-2011112371 A1 | 9/2011 | |
| WO | WO-2011150238 A1 | 12/2011 | |
| WO | WO-2013066974 A1 | 5/2013 | |
| WO | WO-2013074525 A1 | 5/2013 | |
| WO | WO-2014/100109 A1 | 6/2014 | |
| WO | WO-2014151766 A1 | 9/2014 | |

OTHER PUBLICATIONS

International Search Report and Written Opinion mailed Mar. 6, 2013 for PCT/US2012/062738 which claims benefit of U.S. Appl. No. 13/288,459 filed Nov. 3, 2011.

International Preliminary Report on Patentability mailed Sep. 20, 2012 for PCT/US2011/026349 which claims benefit of U.S. Appl. No. 12/719,337 filed Mar. 8, 2010.

International Preliminary Report on Patentability mailed Dec. 6, 2012 for PCT/US2011/038188 claiming benefit of 12/788,966 filed May 27, 2010.

International Preliminary Report on Patentability and Written Opinion mailed Nov. 28, 2013 for PCT/US2012/037703, which claims benefit of U.S. Appl. No. 13/109,672, filed May 17, 2011, and U.S. Appl. No. 13/109,667 filed May 17, 2011.

International Search Report and Written Opinion mailed Mar. 6, 2014 for PCT/US2013/075989 which claims benefit of U.S. Appl. No. 13/720,648, filed Dec. 19, 2012.

International Preliminary Report on Patentability and Written Opinion mailed May 30, 2014 for PCT/US2012/064832 which claims benefit of U.S. Appl. No. 13/295,126, filed Nov. 14, 2011.

International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.

US 6,238,418, 5/2001, Schwartz et al. (withdrawn).

"Do your next distal tendon repair with . . . The Lubbers Technique", Teno Fix® brochure, 2003 (2 pages) Ortheon® Medical.

(56) References Cited

OTHER PUBLICATIONS

"EZ Loc Femoral Fixation Device," copyright 2005 Arthrotek, Inc. (8 sheets).
"Make your next tendon repair an open-and-shut case. The Teno Fix® Tendon Repair System", Teno Fix® brochure, 2003 (2 pages) Ortheon® Medical.
"Panalok Anchor with PDS II and Ethibond Suture", Mitek Products Ethicon, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device.
Arthrotek, A Biomet Company; Sure fire Hybrid Meniscal Device; Launch Date: Fall AANA 2004.
Bio-Intrafix (TCP/PLA & Intrafix, Tibial Soft Tissue Fasteners, by DePuy Mitek, 6 sheets, (date unknown).
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 (Oct.), 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Invitation to Pay Additional Fees mailed Jun. 9, 2011 for PCT/US2011/026349 claiming benefit of U.S. Appl. No. 12/938,902, filed Nov. 3, 2010; and U.S Appl. No. 12/719,337, filed Mar. 8, 2010.
"Arthroscopic Meniscal Repair using the Meniscal Cinch™", Surgical Technique brochure. (2008) Arthrex® 6 sheets.
Pioneer® Sternal Cable System (2010).
Rapid Sternal Closure (2006) KLS Martin L.P. http://www.rapidstrnalclosure.com/medical/demo.php Web accessed Sep. 8, 2008.
Saxena, Pankaj, MCh, DNB et al., "Use of Double Wires in Sternal Closure, A Useful Technique," Texas Heart® Institute. Journal List>Tex Heart Inst J > v.33(4); (2006).
Zeitani, Jacob, M.D., "A New Sternal Reinforcement Device to Prevent and Treat Sternal Dehiscence," CTSNet.org (Jun. 30, 2008).
"AperFix® System Surgical Technique Guide. Single Tunnel Double Bundle.™" Cayenne Medical brochure. (Aug. 2008) 8 sheets.
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jul. 19, 2012, for PCT/US2012/037703 claiming benefit of U.S. Appl. No. 13/109,667, filed May 7, 2011.
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.

\* cited by examiner

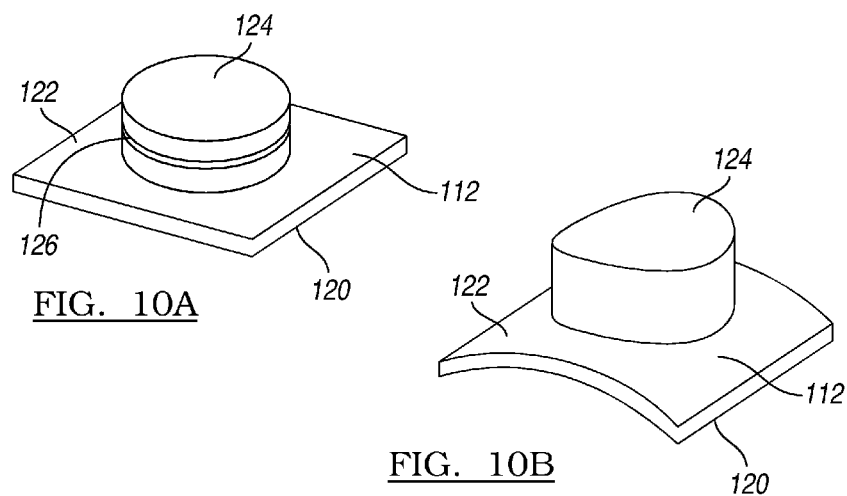
FIG. 10A
FIG. 10B
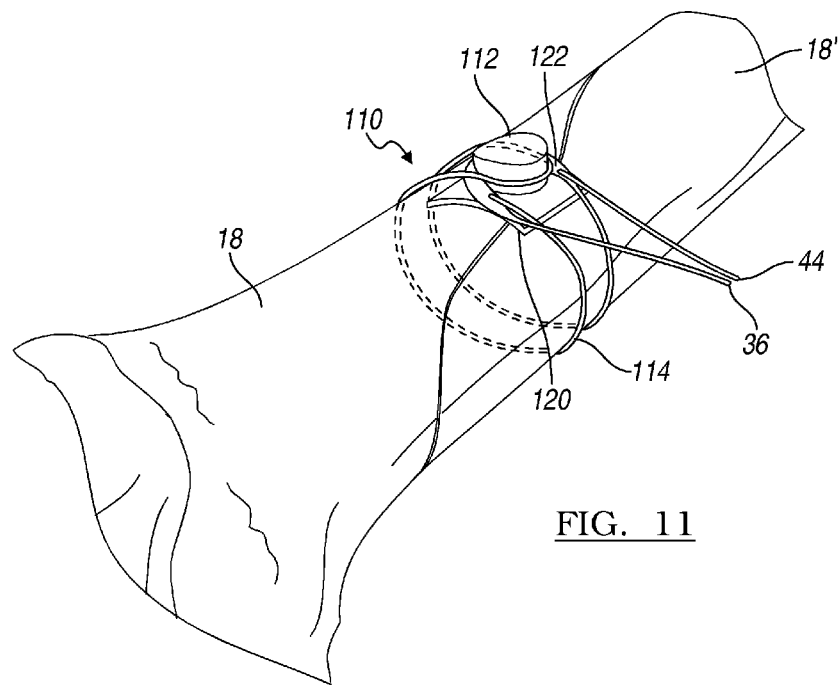
FIG. 11

# US 9,078,644 B2

FRACTURE FIXATION DEVICE

CROSS-RELATED APPLICATIONS

This application is a continuation-in-part of U.S. patent application Ser. No. 12/489,168 filed on Jun. 22, 2009, which is a continuation-in-part of U.S. patent application Ser. No. 12/474,802 filed on May 29, 2009, which is a continuation-in-part of (a) U.S. patent application Ser. No. 12/196,405 filed on Aug. 22, 2008; (b) U.S. patent application Ser. No. 12/196,407 filed on Aug. 22, 2008; (c) U.S. patent application Ser. No. 12/196,410 filed on Aug. 22, 2008; and (d) a continuation-in-part of U.S. patent application Ser. No. 11/541,506 filed on Sep. 29, 2006, which is now U.S. Pat. No. 7,601,165 issued on Oct. 13, 2009.

This application is a continuation-in-part of U.S. patent application Ser. No. 12/570,854 filed on Sep. 30, 2009, which is a continuation-in-part of U.S. patent application Ser. No. 12/014,399 filed on Jan. 15, 2008.

This application is a continuation-in-part of U.S. patent application Ser. No. 12/702,067 filed on Feb. 8, 2010, which is a continuation of U.S. patent application Ser. No. 11/541,505 filed on Sep. 29, 2006 and is now U.S. Pat. No. 7,658,751 issued on Feb. 9, 2010.

This application is a continuation-in-part of U.S. patent application Ser. No. 12/196,398 filed Aug. 22, 2008, which is a continuation-in-part of U.S. patent application Ser. No. 11/784,821 filed Apr. 10, 2007.

The disclosures of all the above applications are incorporated by reference herein.

FIELD

The present disclosure relates to devices and methods for fracture fixation, and more particularly to holding bone fragments together to permit healing.

BACKGROUND

The statements in this section merely provide background information related to the present disclosure and may not constitute prior art.

After trauma or surgical intervention, there may be a need to fix bone fragments together to immobilize the fragments and permit healing. Compressive force can be applied to the bone fragments by encircling the bone fragments or bridging the fragments together across a broken or otherwise compromised portion of the bone. The compressive forces should be applied such that upon ingrowth of new bone, the fragments will heal together and restore strength to the trauma or surgical intervention site.

Accordingly, there is a need for apparatus and methods to apply compressive force to a bone to affect healing. Further, there is a need for an apparatus and related methods which are easy to use intraoperatively to accommodate various bone sizes, shapes, or locations of fractures.

SUMMARY

In various embodiments, the present teachings provide an assembly for securing a fractured or weakened bone within a subject. The assembly includes a frame having a first flexible member holder and a second flexible member holder and an adjustable flexible member construct having first and second ends which are passed through first and second openings associated with a longitudinal passage to form a loop, wherein the longitudinal passage is pre-disposed in at least one of the flexible member holders of the frame.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIGS. 10A and 10B depict a frame having a post extending therefrom according to the present teachings;

FIG. 11 depicts a frame having a post extending therefrom used in an assembly according to the present teachings;

DETAILED DESCRIPTION

Figure 1:
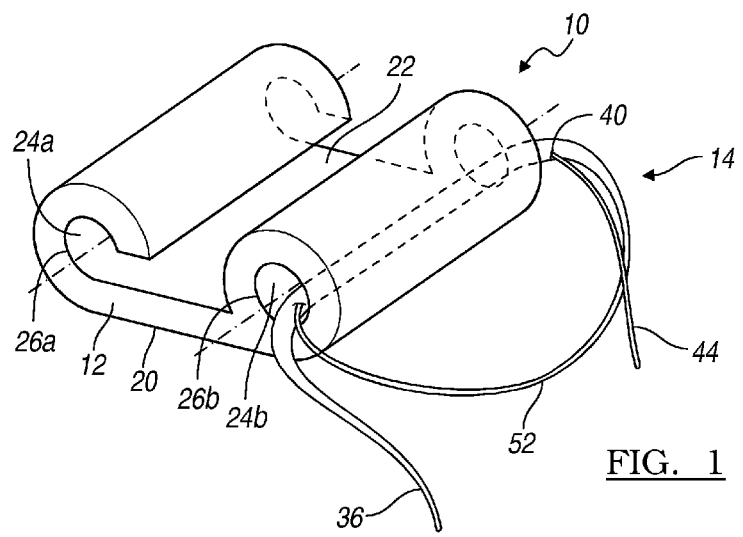
FIG. 1 depicts an assembly having a closed flexible member holder and an open flexible member holder according to the present teachings.

The following description is merely exemplary in nature and is not intended to limit the present disclosure, application, or uses. It should be understood that throughout the drawings, corresponding reference numerals indicate like or corresponding parts and features. While the present disclosure relates to fracture fixation, the apparatus and methods of the present teachings can be used with other orthopedic and non-orthopedic procedures as well.

Figure 2:
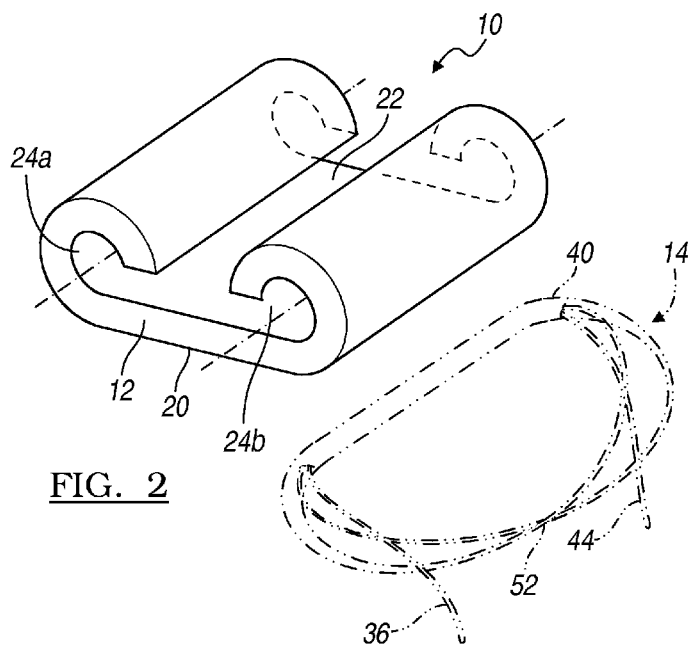
FIG. 2 depicts a frame having two open flexible member holders and an adjustable flexible member construct according to the present teachings.
Figure 3:
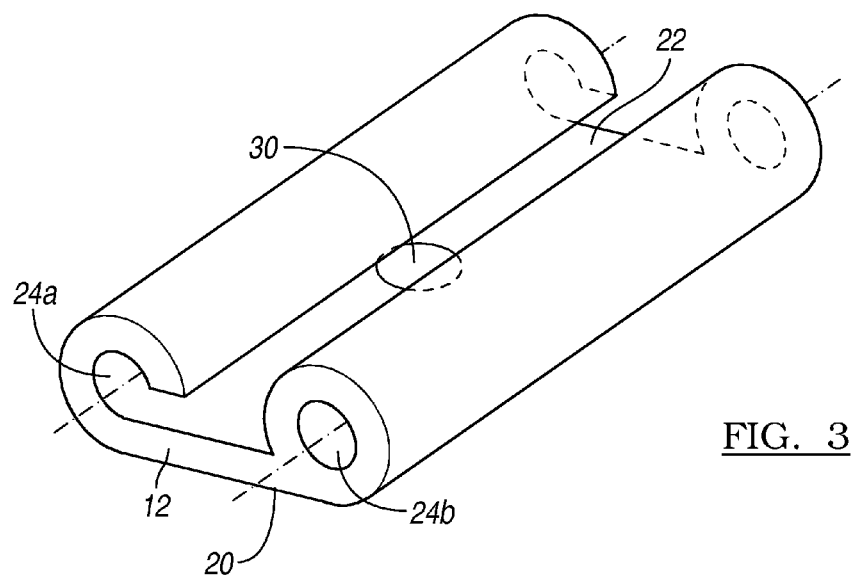
FIG. 3 depicts an elongated frame according to the present teachings.
Figure 7:
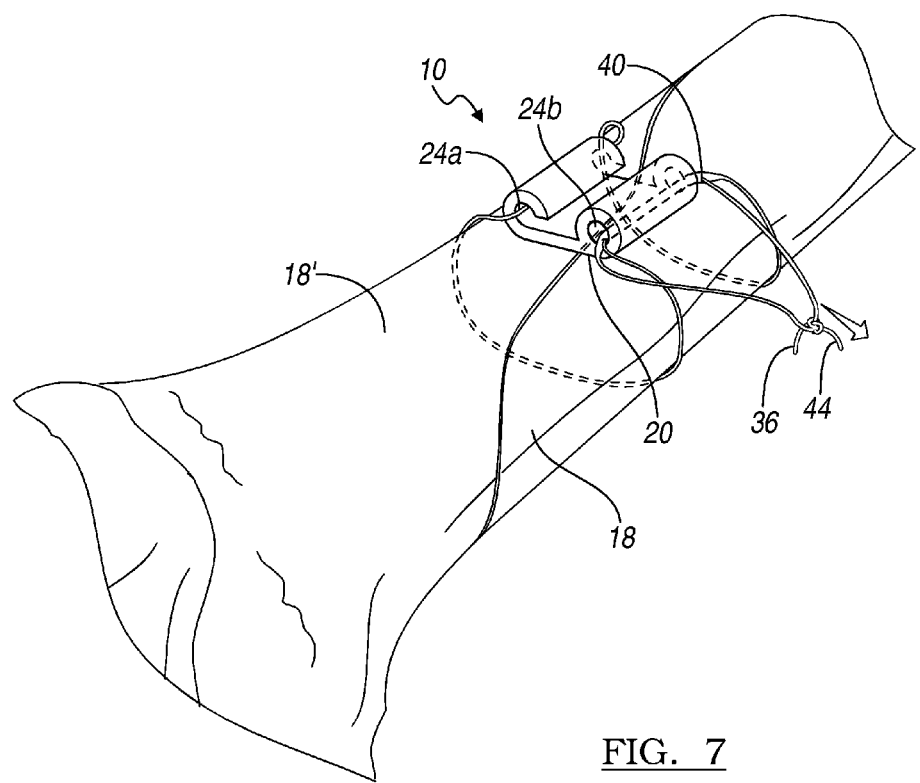
FIG. 7 depicts an assembly compressing a fractured or weakened bone according to the present teachings.

Referring to FIGS. 1 and 2, an assembly 10 is provided according to various embodiments of the present teachings. The assembly 10 includes a frame 12 and an adjustable flexible member construct 14. As further detailed below and as depicted in FIG. 7, regions of the adjustable flexible member construct 14 are partially disposed in the frame 12 such that the adjustable flexible member construct 14 and the frame encircle a bone 16 having fragments 18 and 18' due to surgical intervention, injury, or disease. While the present disclosure may exemplify a fractured bone, it is understood that any of the reasons for bone compromise may be used with the present teachings. It is further understood that the frame 12 can be used in connection with other frames that are placed on a different or opposing face of the bone. The various embodiments disclosed herein can also be used to stabilize other implants, such as those used in revision surgery or for oncological purposes.

In various embodiments, the assembly 10, assembly 110 as detailed later herein, or the adjustable flexible member construct 14 alone is used to compresses the respective fragments together and to affect healing at the compromised bone 16. Bones suitable for use with the present teachings include any bone in the body, such as the vertebrae, long bones of the arms, legs or fingers; curved bones, such as the ribs; flat bones, such as those of the wrist or feet, for example, and the like. Any bones of the legs, arms, torso, hands, feet, head, are suitable for use with the apparatus and methods of the present teachings.

Referring to FIGS. 1 through 5C, the frame 12 includes a lower surface 20, an upper surface 22, and at least flexible member holders 24A and 24B defined by projections on the upper surface 22. In various embodiments, the frame 12 can be a one-piece, integral, monolithic structure. In various embodiments, the frame 12 can be made of a generally rigid material. The frame 12 can be made of a plastic or polymeric material, a metal, or a composite thereof. The frame 12 can be generally rectangular or square, or the frame 12 can be a rounded shape or a site-specific shape. For example, the lower surface 20 can be curved to conform to the desired bone. The frame 12 can be of a sufficient length to span across a region of both fragments 18 and 18'. The frame 12 can also span the entirety of the fractured area of the bone 16 and cover healthy adjacent bone 16, or the frame can be smaller than the fractured area of the bone 16. The frame 12 can also be elongated such that it spans beyond the length of the fracture or weakened area, such as the frames 12 shown in FIGS. 3 and 4.

Figure 4:
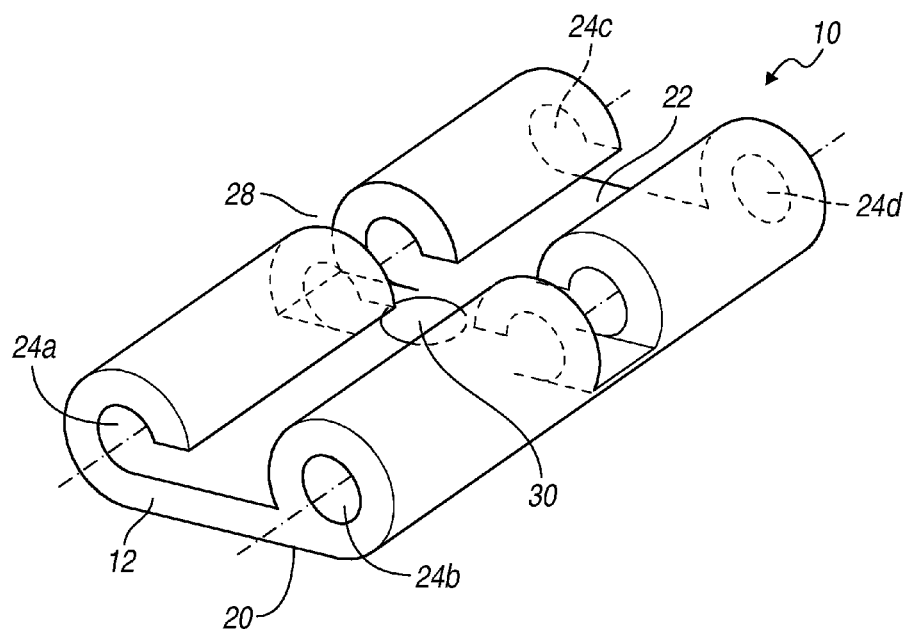
FIG. 4 depicts an elongated frame having a plurality of flexible member holders according to the present teachings.
Figure 8:
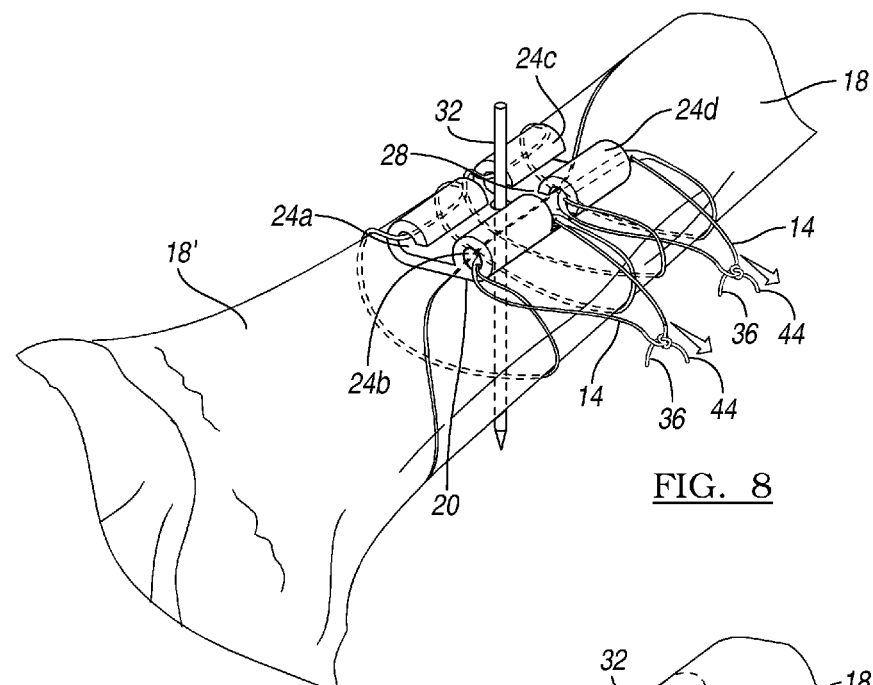
FIG. 8 depicts an assembly compressing a fractured or weakened bone according to the present teachings.

The frame lower surface 20 can include a flat surface or the lower surface 20 can be curved to accommodate the contour of the bone 16. The upper surface 22 of the frame 12 partially defines the openings 26A and 26B for the flexible member holders 24A and 24B, respectively. The flexible member holders 24A and 24B can be channels, a post, a pin, a hole, or other means by which to retain a flexible member on the frame 12. It is understood that the flexible member holders 24A and 24B need not be formed on the upper surface 22 and that the flexible member holders 24A and 24B can extend from the lower surface 20 and around the upper surface 22. As shown in FIGS. 4 and 8, the frame 12 can include a plurality of flexible member holders 24A-24D which can be separated by a space 28 between the sets of flexible member holders 24C and 24A, and 24D and 24B. Although various embodiments disclosed may relate to only two flexible member holders, it is understood that the processes of use are generally the same for assemblies having 2 through 8, or more flexible member holders.

Any of the flexible member holders 24A-24D can be open such that the adjustable flexible member construct 14 can be repeatedly manually placed and removed, or the flexible member holders 24A-24D can be closed such that the adjustable flexible member construct 14 is permanently housed therein and cannot be inadvertently removed without disassembling the adjustable flexible member construct 14. The flexible member holders 24A-24D can be sized to allow the adjustable flexible member construct 14 to freely slide therein. The flexible member holders 24A-24D can be preformed to be closed or can be initially provided as an open and subsequently crimped or pinched closed. FIG. 1 depicts the frame having an open flexible member holder 24A and a closed flexible member holder 24B while FIG. 2 depicts two open flexible member holders 24A and 24B.

In various embodiments, the flexible member holders 24A and 24B face each other or are opposed. This allows for the adjustable flexible member construct 14 to be disposed in a first flexible member holder, for example flexible member holder 24B, wrapped around the bone 16, and then be disposed in the other flexible member holder, for example flexible member holder 24A, and tightened when the flexible member construct 14 is engaged such that opposing force is applied to the opposing flexible member holder to provide compression.

Figure 5A:
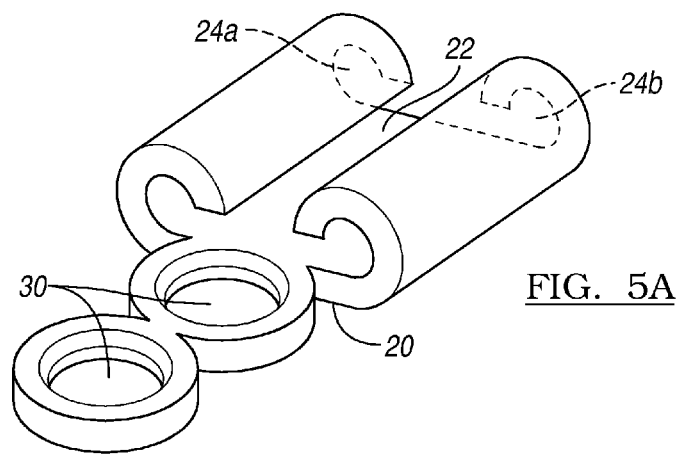
FIGS. 5A through 5C depict frames defining openings to receive fasteners according to the present teachings.
Figure 5B:
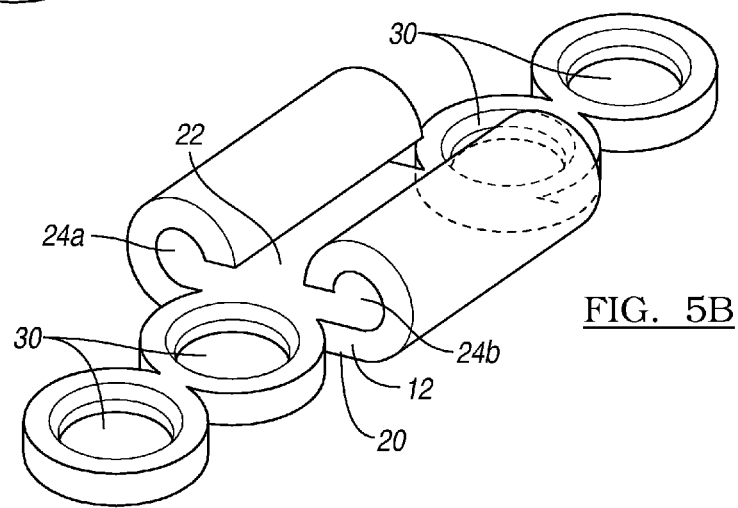
Figure 5C:
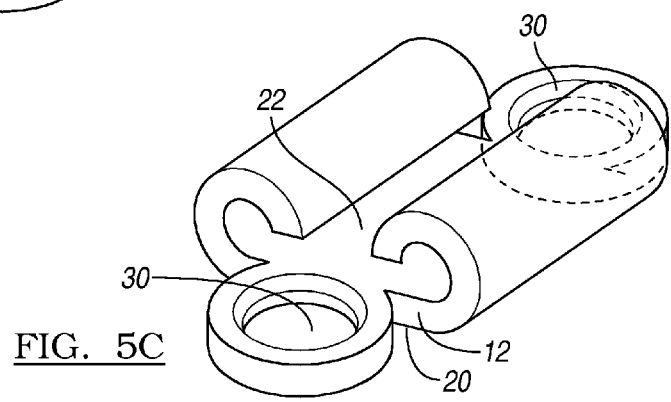
Figure 9:
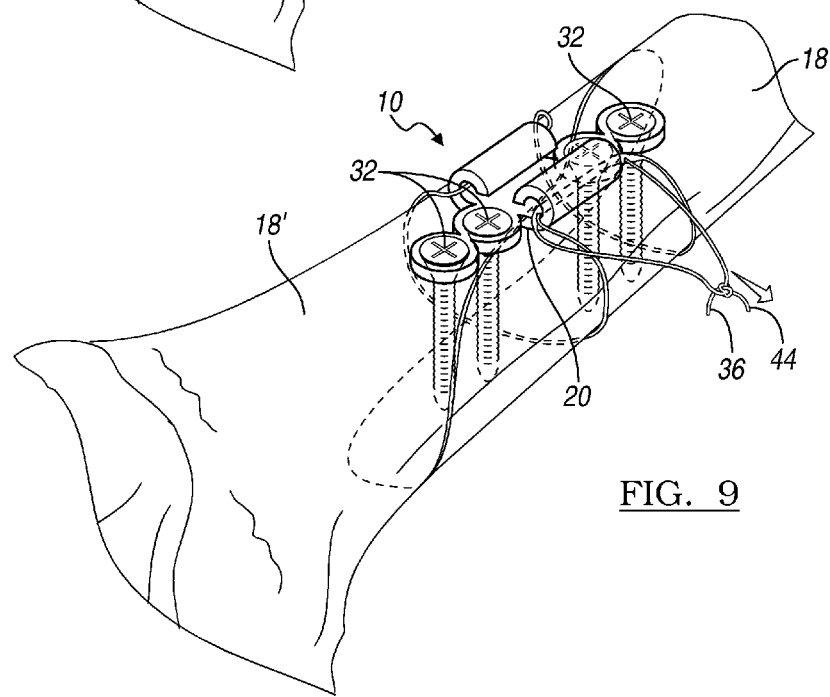
FIG. 9 depicts an assembly compressing a fractured or weakened bone according to the present teachings.

As shown in FIGS. 3 through 5C and FIGS. 8 and 9, the frame 12 can define at least one opening 30 in which to attach a fastener 32 such as a pin, screw, spike, or a combination or variation thereof to bone. The frame 12 can include a plurality of fastener openings 30 to accommodate multiples of the same or different fasteners 32. The fastener openings 30 can be placed along the periphery of the frame 12 as shown in FIGS. 5A through 5C, or the fastener openings 30 can cut through the lower surface 20 and upper surface 22 of the frame 12. The fastener openings 30 can be evenly placed on or about the frame 12, as shown in FIG. 5B and FIG. 9, or they can be asymmetrically placed on or about the frame 12, as shown in FIG. 5A. It is understood that the fastener openings 30 can be placed anywhere along the frame 12 at any angle and can be placed within the interior of the frame 12.

Figure 6A:
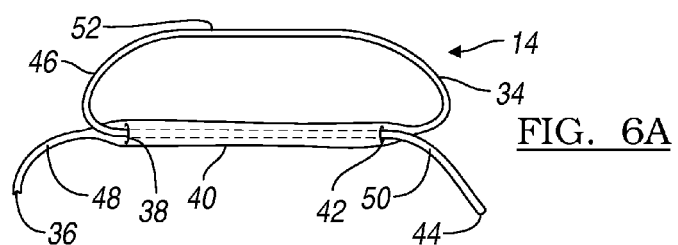
FIGS. 6A and 6B depict adjustable flexible member constructs according to the present teachings.
Figure 6B:
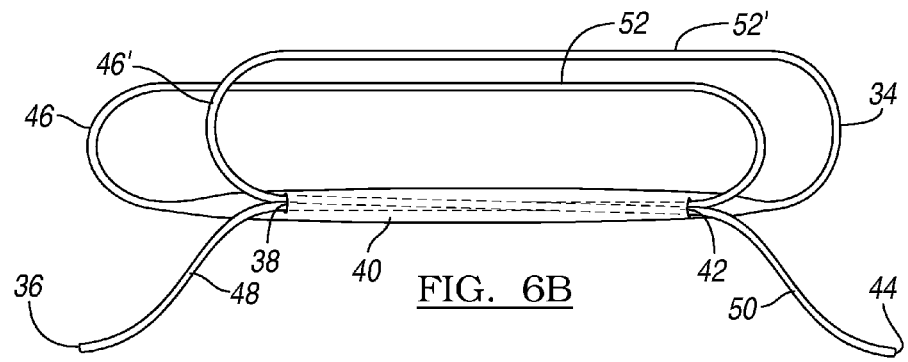

Referring to FIG. 1, the frame 12 can be used to hold the adjustable flexible member construct 14 as depicted in FIGS. 6A and 6B. The adjustable flexible member construct 14 is fashioned from a flexible member 34 made of any biocompatible material that is flexible and can fold around and secure a bone 16. Exemplary materials include, but are not limited to, non-resorbable polymers, such as polyethylene or polyester, resorbable polymers, metals, and various combinations thereof. The materials can include those formed into a monofilament, multiple filaments, cables, and the like. In various embodiments, the adjustable flexible member construct 14 is made of a hollow material to allow for the appropriate folding and tensioning. In various embodiments, the adjustable flexible member construct 14 can be a suture. In such embodiments, the suture can be hollow or a braided or multiple-filament suture structure. In various embodiments, the adjustable flexible member construct 14 can define a substantially tubular hollow shape.

To form the adjustable flexible member construct 14, a first end 36 of the flexible member is passed through the first aperture 38 and through longitudinal passage 40 and out a second aperture 42. The second end 44 is passed through the second aperture 42, through the longitudinal passage 40 and out the first aperture 38. In various embodiments, the first and second apertures 38 and 42 are formed during the braiding process as loose portions between pairs of fibers defining the flexible member 34. Passing the ends 36 and 44 through the apertures 38 and 42 forms loops 46 and 46'. The longitudinal and parallel placement and advancement of the first and second ends 36 and 44 of the flexible member 34 within the longitudinal passage 40 resists the reverse relative movement of the first and second portions 48 and 50 of the flexible member 34 once it is tightened. A further discussion of the flexible member construct is provided in U.S. patent Ser. No. 11/541,506 filed on Sep. 29, 2006 entitled "Method And Apparatus For Forming A Self-Locking Adjustable Suture Loop" assigned to Biomet Sports Medicine, Inc., and the disclosure is incorporated by reference.

The loops 46 and 46' define mounts or summits 52 and 52' of the adjustable flexible member construct 14 and are disposed opposite from the longitudinal passage 40 such that when the summit 52 is disposed in a first flexible member holder 24A and the longitudinal passage 40 is disposed in a second flexible member holder 24B, the summit 52 and the longitudinal passage 40 remain stationary with respect to the frame 12, while the overall diameter of the adjustable flexible member construct 14 is decreased to compress the bone fragments 18 and 18'.

The tensioning of the ends 36 and 44 cause relative translation of the sides of the flexible member 34 with respect to each other. Upon applying tension to the first and second ends 36 and 44 of the flexible member 34, the size of the loop(s) 46 is reduced to a desired size or load. The flexible member 34 locks without knots due to the tensioning placed on the first and second ends 36 and 44. At this point, additional tension causes the body of the flexible member defining the longitudinal passage 40 to constrict about the portions 48 and 50 of the flexible members within the longitudinal passage 40. This constriction reduces the diameter of the longitudinal passage 40, thus forming a mechanical interface between the exterior surfaces of the first and second portions 48 and 50, as well as the interior surface of the longitudinal passage 40. This constriction causes the adjustable flexible member to "automatically" lock in a reduced or smaller diameter position.

In use, the assembly 10 is formed by coupling the adjustable flexible member construct 14 to the frame 12. The lower surface 20 is placed such that it abuts the bone fragments 18 and 18'. In embodiments where at least one flexible member holder 24A or 24B is closed, the summit 52 is placed in the open flexible member holder 24B opposite the longitudinal passage 40 disposed in the opposing closed flexible member holder 24A. The flexible member free ends 36 and 44 are engaged and pulled in the direction of the arrow shown in FIG. 7 such that the diameter of the loop 46 is reduced and the bone fragments 18 and 18' are compressed. In embodiments where the longitudinal passage 40 is not pre-disposed in the closed flexible member holder 24A or where both flexible member holders are open, the longitudinal passage 40 and the summit 52 are placed in the respective, opposing flexible member holder and then the free ends 36 and 44 are engaged to tighten the adjustable flexible member construct 14 and secure the bone fragments 18 and 18'. No additional steps, such as knot tying, are required to secure the adjustable flexible member due to the automatic locking feature.

Turning to FIGS. 10A through 15C, in still other embodiments, an assembly 110 is provided. The assembly 110 shares several similarities with the assembly 10 detailed above. It is understood that the assembly 110 and the assembly 10 can have interchangeable features and the discussion of separate features on the respective assemblies is not intended to be a limitation of the present teachings.

The assembly 110 includes a frame 112 and an adjustable flexible member construct 114. The frame 112 includes a lower surface 120, an upper surface 122, and at least one flexible member holder, depicted as a post 124, thereon about which the adjustable flexible member construct 114 can be secured.

The post 124 sits proud to the upper surface 122 of the frame. The post 124 can be centered on the frame 112, or the post 124 can be placed at an off-center point on the frame 112. The post 124 can be generally smooth and cylindrical as shown in FIGS. 10A and 10B, or the post 124 can be a squared or have any other suitable geometry. The post 124 can include surface features by which the adjustable flexible member construct 114 can be disposed in or through, such as a notch, under cut, groove, or throughbore. An exemplary under cut 126 is shown in FIG. 10A.

Figure 12:
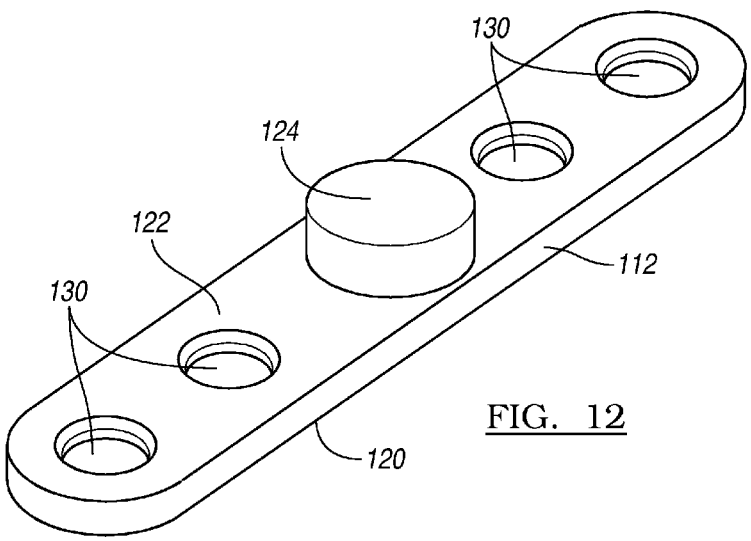
FIG. 12 depicts a frame having a post extending therefrom where the frame defines a plurality of openings to receive at least one fastener according to the present teachings.
Figure 13:
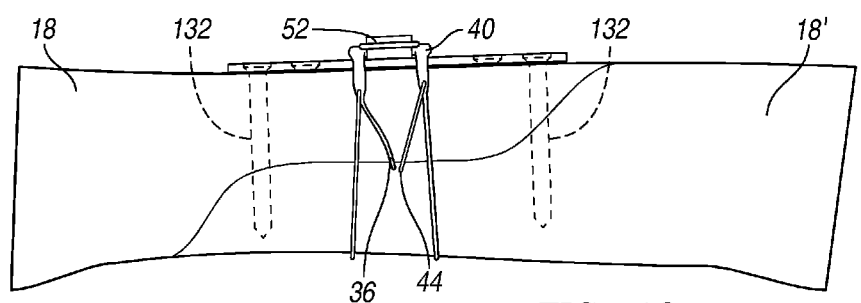
FIG. 13 depicts a side view of a surgical method according to the present teachings.
Figure 14:
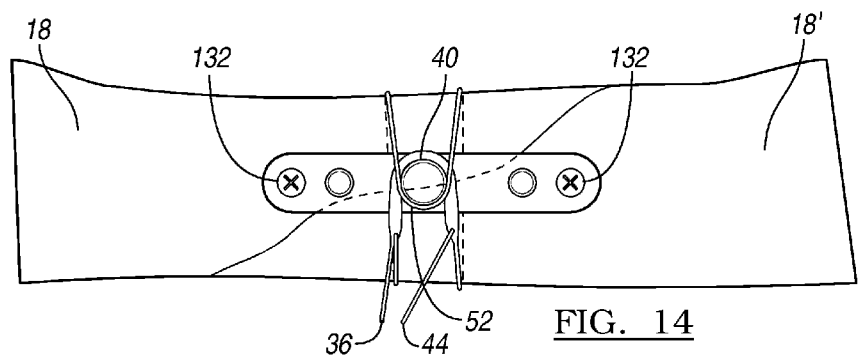
FIG. 14 depicts a top view of a surgical method according to the present teachings.

The frame 112 can have a flat profile or the frame 112 can have a slightly curved profile, such as those shown in FIGS. 10A and 10B, respectively. As shown in FIG. 12, for example, the frame 112 can define openings 130 to receive fasteners 132 such as those detailed earlier herein. Although a plurality of evenly spaced fastener openings 130 are depicted on the frame 112 in FIG. 12, it is understood that the fastener openings 130 can be placed anywhere along the periphery of the frame 112, can be placed through the center of the post 124, or can be asymmetrically placed. The fastener openings 130 can also be threaded to receive screws. In various embodiments, the fastener openings 130 can include both machine threads and bone engaging threads.

In use, the lower surface of the frame 112 is placed against the bone fragments 18 and 18'. Either of the summit 52 or the longitudinal passage 40 of the adjustable flexible member construct 14 is disposed about the post 124. The other of the summit 52 or the longitudinal passage 40 is partially circled about the bone 16 and is disposed on the opposite side of the post 124. In embodiments where the post 124 includes a notch 126, the adjustable flexible member construct 14 can be disposed in the notch 126 during the wrapping process. The ends 36 and 44 of the adjustable flexible member construct 14 are engaged to reduce the diameter of the adjustable flexible member construct 14 about the bone 16 and thereby compress the bone fragments 18 and 18'.

Figure 15A:
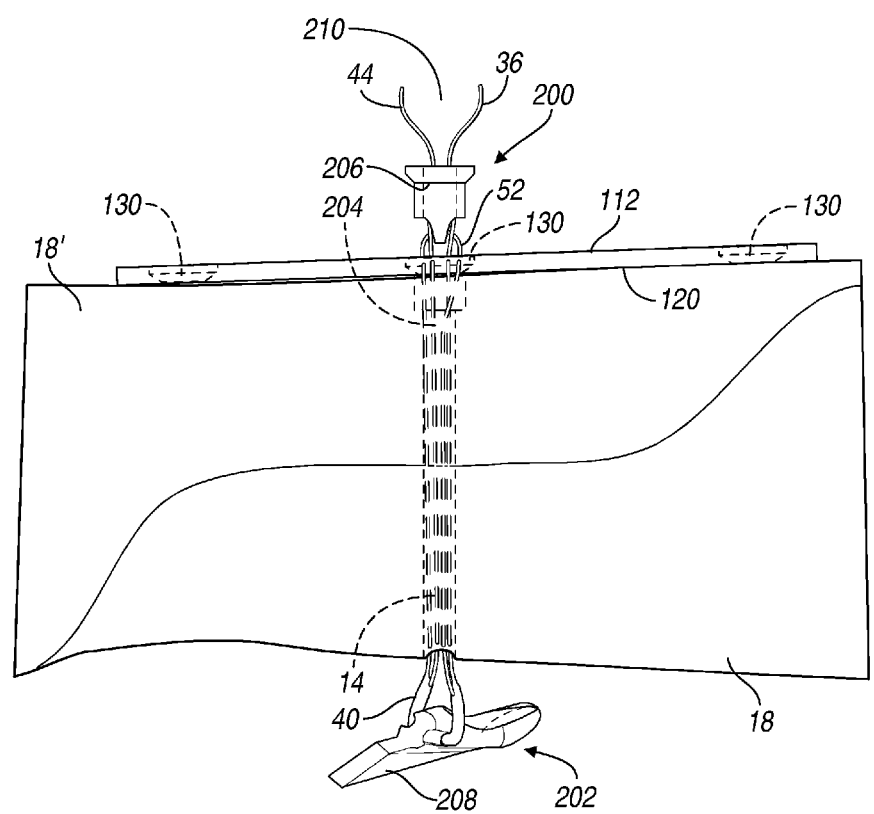
FIGS. 15A-15C depict side views of fixation of a fracture in surgical methods according to the present teachings.
Figure 15B:
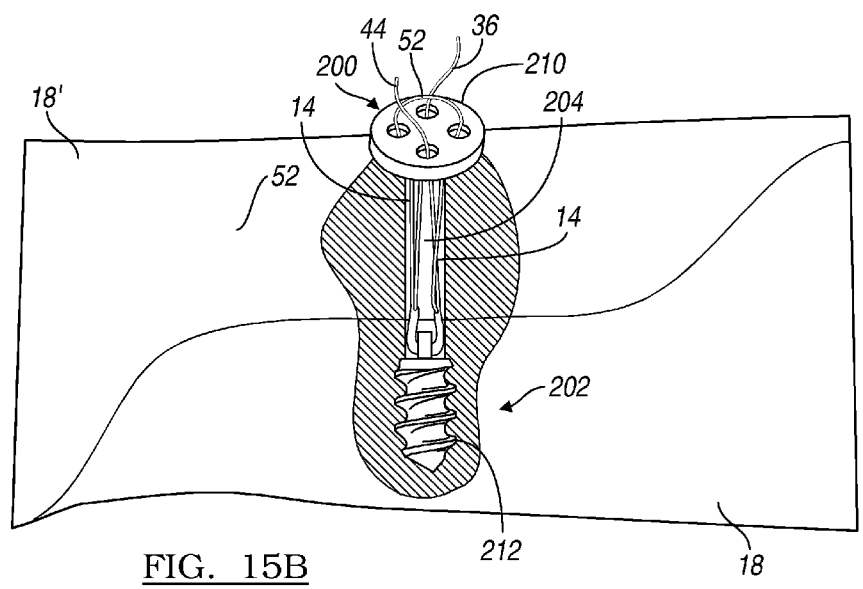
Figure 15C:
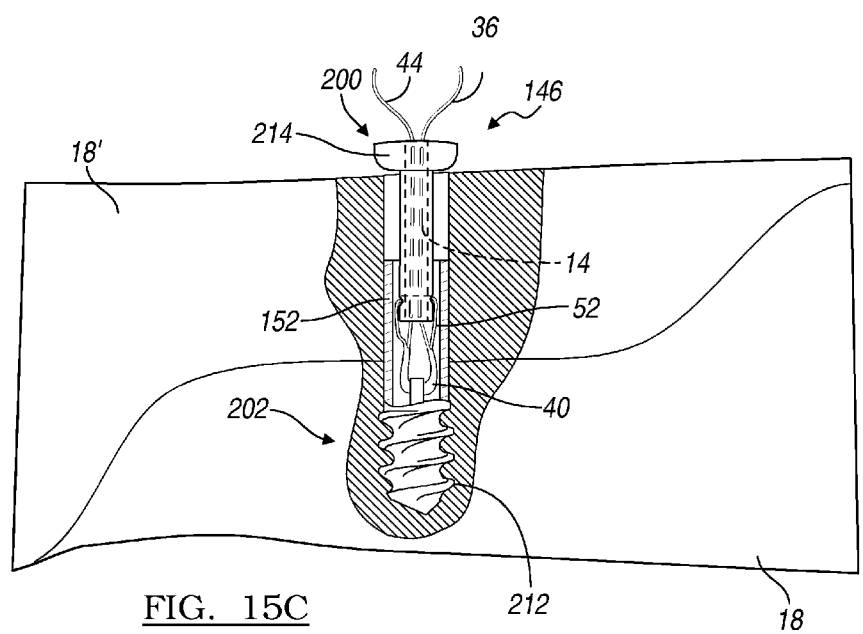

Turning to FIGS. 15A-15C, in various embodiments, the assembly 210 can include an upper fixation element 200 and a lower fixation element 202 having the adjustable flexible member construct spanning therebetween through an opening 204 formed in the bone fragments 18 and 18'. The upper fixation element 200 and lower fixation element 202 can independently be selected from a grommet 206, a toggle 208, a button 210, a screw tip 212, a screw head 214, or other similar items.

As shown in FIG. 15A, the upper fixation element 200 is a grommet 206 and the lower fixation element is a toggle 208. The toggle 208 is used to hold the longitudinal passage 40 of the adjustable flexible member construct 14 and the opposing region is contained by the grommet 206 in bone fragment 18. The adjusting arms 36 and 44 are also passed through the grommet 206 and can be pulled to tighten the adjustable flexible member construct 14 and compress the bone fragments 18 and 18' together. The upper fixation element 200 and lower fixation element 202 are shown in connection with a fixation plate 112 where the grommet 206 is disposed in the opening 130 in the fixation plate 112. It is understood that the plate 112 can be used with either of the upper fixation element 200 or the lower fixation element 202.

FIGS. 15B and 15C depict assemblies without the fixation plate 112 shown in FIG. 15A. Similar to the previously discussed embodiment, an opening 204 is prepared in the bone fragments 18 and 18'. The opening 204 is a partial opening and does not extend all of the way through both bone fragments 18 and 18'. With specific reference to FIG. 15B, a button 210 is used as the upper fixation element 200, and a screw tip 212 serves as the lower fixation element 202. The screw tip 212 retains the longitudinal passage 40 of the adjustable flexible member construct 14 and is fixed into the bone fragment 18. At least the free ends 36 and 44 and the summit 52 of the adjustable flexible member construct 14 are disposed through the button 210, through lacing for example, and can be adjusted to provide the secured fit and bone fragment 18 and 18' fixation.

Turning to FIG. 15C, the upper fixation element 200 is depicted as a telescoping screw head 214, and the lower fixation element 202 is a screw tip 212. The screw tip 212 is fixed in the bone fragment 18 and retains the longitudinal passage 40 of the adjustable flexible member construct 14. The telescoping screw head 214 is used to retain the summit 52 and the adjustable free ends 36 and 44 of the adjustable flexible member construct 14 and can be compressed into the distally placed screw tip 212 to secure the fracture.

The present teachings further provide methods for securing a fractured or weakened bone 16 within a patient's body. The frame 12 is abutted against the fractured or weakened bone 16 such that the lower surface 20 sits against the bone. The frame 12 can be positioned to span across both sides of the fracture. The summit 52 or the longitudinal passage 40 is disposed in one of the flexible member holders 24A or 24B defined by the frame 12. The fractured or weakened bone 16 is then encircled by partially wrapping the adjustable flexible member construct 14 at least partially contained in the frame about the bone. The other of the summit 52 or the longitudinal passage 40 is fixed in the second, opposing flexible member holder 24B. In embodiments where a plurality of frames 12 or a plurality of flexible member holders 24A-24D are provided on a frame 12, the process can be repeated by employing several adjustable flexible member constructs 14 in various sets of flexible member holders, for example the set 24A/24C and the set 24B/24D of FIG. 4 and FIG. 8. The process can also be repeated by wrapping a single adjustable flexible member construct 14 about the area to engage several flexible member holders on the different frames, such as where the frames are used in tandem across a fractured or weakened bone.

The ends 36 and 44 of the adjustable flexible member construct 14 are engaged or pulled to reduce the size of the loop 46 and to cause the summit 52 and the longitudinal passage to press against the respective opposed flexible member holders. This compresses the bone fragments 18 and 18' at the compromised site. In embodiments where the frame 12 is made of a rigid material, engaging the free ends 36 and 44 does not cause the frame 12 to stretch, lengthen, or otherwise increase in size, thereby allowing for tighter compression. In embodiments utilizing fasteners 32 or 132, the fasteners can be secured to the bone fragments, 18 and 18' before or after the adjustable flexible member construct 14 is reduced about the bone 16. The flexible member constructs allow additional tensioning of each individual flexible member construct independently, so as to avoid any laxity that may occur to a flexible member construct as others are tightened.

Figure 16A:
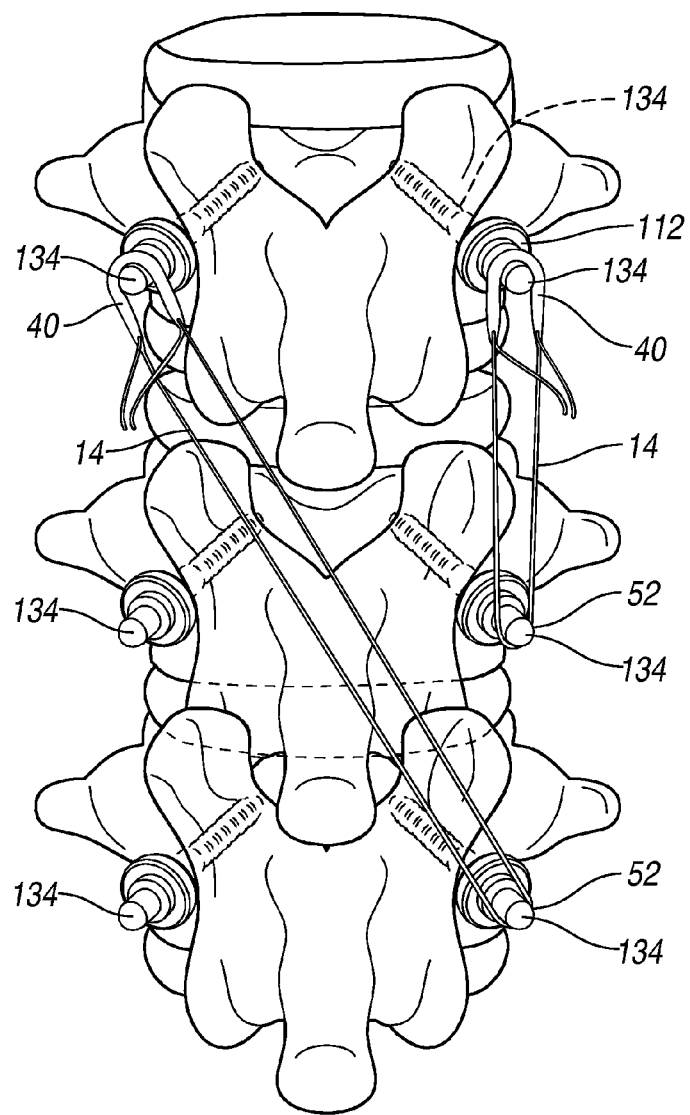
FIGS. 16A and 16B depict a spinal repair using apparatus according to the present teachings.
Figure 16B:
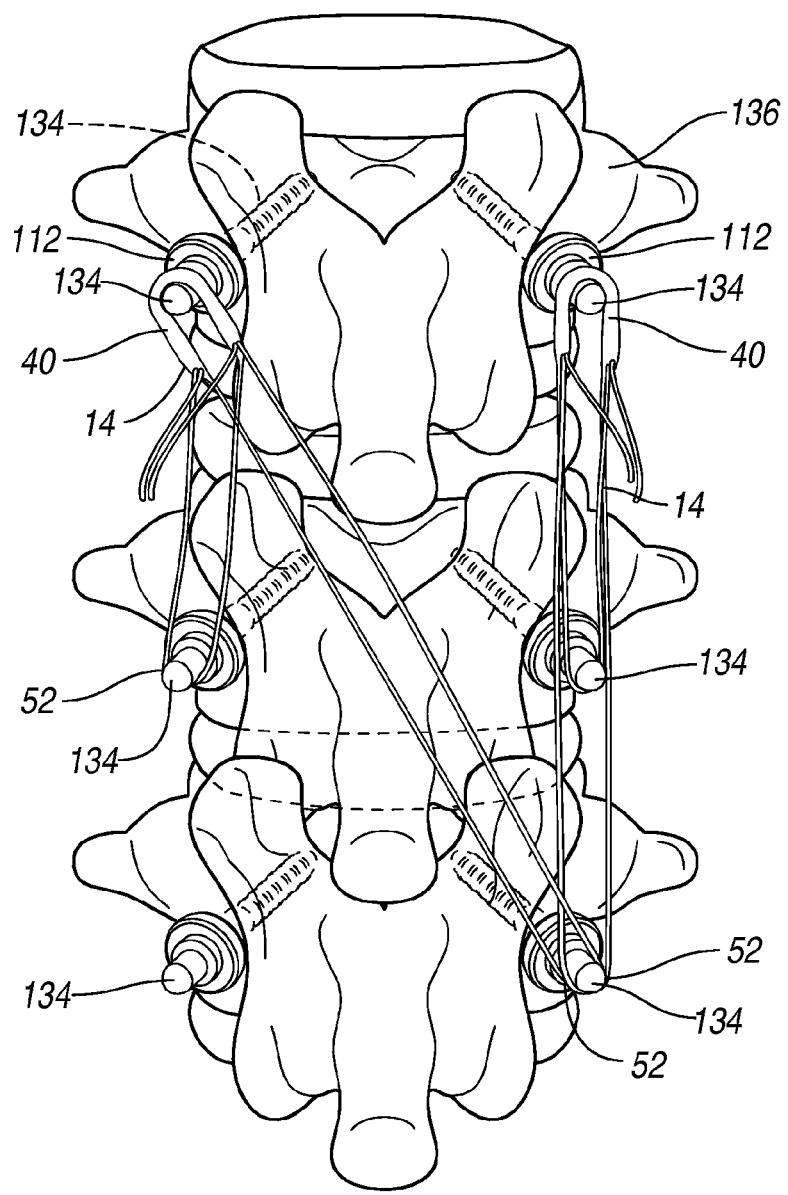

In still further embodiments such as those shown in FIGS. 16A and 16B, the frame 112 can be attached via a pedicle screw 134 which is affixed to vertebra 136. The pedicle screw 134 is passed through the fastener opening 130 which is defined by the post 124. The pedicle screws 134 can be linked together using the adjustable flexible member construct 14. As shown in FIG. 16B, a single adjustable flexible member construct 14 can be attached to two or more assemblies 10. Alternatively, as shown in FIGS. 16A and 16B, multiple adjustable flexible member constructs 14 can be attached to one or more pedicle screws 134.

The description of the invention is merely exemplary in nature and, thus, variations that do not depart from the gist of the invention are intended to be within the scope of the invention. For example, any of the above mentioned surgical procedures is applicable to the repair of other body portions. For example, the procedures can be equally applied to orthopedic repair of wrists, fingers, legs, ankles, and other bones and also to non-orthopedic repairs. Such variations are not to be regarded as a departure from the spirit and scope of the invention.

What is claimed is:

1. An assembly for securing a fractured or weakened bone within a patient's body comprising:
   a frame having at least one flexible member holder and defining an opening;
   a fastener configured to extend through the opening in the frame to secure the frame to the bone; and
   an adjustable flexible member construct disposed about the at least one flexible member holder to form an adjustable loop;
   wherein the adjustable flexible member construct includes an adjustable flexible member having first and second ends, a longitudinal passage portion, and first and second openings associated with the passage portion, wherein the first and second ends are passed through the first and second openings to form the adjustable loop, the adjustable loop including a summit positioned opposite of the passage portion;
   wherein the adjustable flexible member construct is configured to be positioned around the bone with the summit and the passage portion connected directly to the flexible member holder of the frame;
   wherein the frame includes a bone engaging surface and an opposed surface, the at least one flexible member holder extending from the opposed surface in a direction away from the bone engaging surface;
   wherein the at least one flexible member holder has a perimeter surface for engaging the passage portion and the summit, and the perimeter surface of the at least one flexible member holder is free of holes.

2. The assembly of claim 1, wherein the flexible member holder is selected from the group consisting of channels, posts, and combinations thereof.

3. The assembly of claim 2, wherein the frame includes a plurality of posts extending therefrom.

4. The assembly of claim 2, wherein the frame includes a plurality of channels.

5. The assembly of claim 4, wherein at least two of the channels are parallel to each other.

6. The assembly of claim 1, wherein the frame further comprises at least one opening to receive the fastener.

7. The assembly of claim 6, wherein the fastener is selected from the group consisting of pins, screws, spikes, and combinations thereof.

8. The assembly of claim 1, wherein the frame comprises a monolithic structure.

9. The assembly of claim 1, wherein the adjustable flexible member construct is automatically tightened upon engaging the ends of the adjustable flexible member.

10. The assembly of claim 1, wherein the frame is formed from a material selected from the group consisting of metallic materials, non-metallic materials, rigid materials, and combinations thereof.

11. The assembly of claim 1, wherein the adjustable flexible member construct comprises a braided or woven structure.

12. The assembly of claim 1, wherein the at least one flexible member holder is a post extending from the frame.

13. The assembly of claim 12, wherein the post includes a surface feature for retaining the adjustable flexible member construct selected from the group consisting of a notch groove, and combinations thereof.

14. The assembly of claim 1, wherein the at least one flexible member holder includes a single post and wherein the passage portion and the summit are each directly connected to the post such that the adjustable flexible member construct is configured to wrap around the bone.

15. An assembly for securing a first portion of bone to a second portion of bone comprising:
   a frame having at least one flexible member holder extending therefrom, the frame defining at least one opening to receive a fastener;
   the fastener, wherein the fastener is configured to extend through the at least one opening in the frame to secure the frame to the bone; and
   an adjustable flexible member construct disposed about the at least one flexible member holder to form an adjustable loop to contain the first portion of bone to the second portion of bone, wherein the adjustable flexible member construct includes an adjustable flexible member having first and second ends and a longitudinal passage extending therethrough, where at least one of the first and second ends is passed through a portion of the longitudinal passage of the adjustable flexible member to form the adjustable loop, the adjustable loop including a summit positioned opposite of the portion of the longitudinal passage;
   wherein the adjustable flexible member construct is configured to be positioned around the first and second portions of the bone with the summit and the portion of the longitudinal passage each connected directly to the flexible member holder of the frame;
   wherein the frame includes a bone engaging surface and an opposed surface, the at least one flexible member holder extending from the opposed surface in a direction away from the bone engaging surface;
   wherein the at least one flexible member holder has a perimeter surface for engaging the portion of the longitudinal passage and the summit, and the perimeter surface of the at least one flexible member holder is free of holes.

16. The assembly of claim 15, wherein the frame is elongated and defines a plurality of openings to receive a plurality of fasteners.

17. The assembly of claim 15, wherein the frame has either a flat profile or a curved profile.

18. The assembly of claim 15, wherein the flexible member holder is selected from the group consisting of channels, posts, and combinations thereof.

19. The assembly of claim 15, wherein the first and second ends of the adjustable flexible member construct pass through the longitudinal passage to form a pair of adjustable loops.

20. The assembly of claim 19, wherein the first end of the adjustable flexible member construct is passed through first and second openings and at least a portion of the longitudinal passage of the flexible member construct to form a first loop and the second end is passed through the second opening and the first opening and a portion of the longitudinal passage of the flexible member construct to form a second adjustable loop.

21. The assembly of claim 15, wherein the at least one flexible member holder includes a single post and wherein the portion of the longitudinal passage and the summit are each directly connected to the post such that the adjustable flexible member construct is configured to wrap around the first and second portions of the bone.

22. An assembly for securing a first portion of bone to a second portion of bone comprising:
   an elongated frame having a bone engaging surface and an opposed surface, at least one post extending from the opposed surface in a direction away from the bone engaging surface, the frame defining a plurality of openings to receive a plurality of fasteners therethrough;
   the plurality of fasteners, wherein the plurality of fasteners are configured to extend through the plurality of openings to secure the frame to the bone; and
   an adjustable flexible member construct disposed about the at least one post to form an adjustable loop to contain the first and second portions of the bone, wherein the adjustable flexible member construct has first and second ends and a longitudinal passage extending from the first and second ends, where at least the first end is passed through first and second apertures and a portion of the longitudinal passage to form the adjustable loop, the adjustable loop including a summit positioned opposite of the portion of the longitudinal passage;
   wherein the adjustable flexible member construct is configured to wrap around the first and second portions of the bone with the summit and the portion of the longitudinal passage each connected directly to the at least one post of the frame;
   wherein the at least one post has a perimeter surface for engaging the portion of the longitudinal passage and the summit, and the perimeter surface of the at least one post is free of holes.

23. The assembly of claim 22, wherein the post includes a surface feature for retaining the adjustable flexible member construct selected from the group consisting of a notch, groove, and combinations thereof.

24. The assembly of claim 22 wherein the adjustable flexible member construct comprises a braided or woven structure and wherein the adjustable flexible member construct includes the first end passed through the first aperture and through the longitudinal passage and out a second aperture and the second end passed through the second aperture through the longitudinal passage and out the first aperture to form first and second adjustable loops.

25. The assembly of claim 22, wherein the frame has either a flat profile or a curved profile.

26. The assembly of claim 22, wherein the at least one post includes a single post and wherein the portion of the longitudinal passage and the summit are each directly connected to the post such that the adjustable flexible member construct is configured to wrap around the first and second portions of the bone.

* * * * *